(12) United States Patent
Klein et al.

(10) Patent No.: US 7,740,624 B2
(45) Date of Patent: Jun. 22, 2010

(54) METHOD FOR TREATING OBESITY BY EXTRACTING FOOD

(75) Inventors: Samuel Klein, Clayton, MO (US); Stephen B. Solomon, New York, NY (US); Moshe Shike, Larchmont, NY (US)

(73) Assignee: Aspiration Medical Technology, LLC, Davie, FL (US)

( * ) Notice: Subject to any disclaimer, the term of this patent is extended or adjusted under 35 U.S.C. 154(b) by 44 days.

(21) Appl. No.: 11/191,466

(22) Filed: Jul. 27, 2005

(65) Prior Publication Data

US 2005/0283130 A1  Dec. 22, 2005

Related U.S. Application Data

(63) Continuation-in-part of application No. 10/702,194, filed on Nov. 4, 2003, now abandoned.

(60) Provisional application No. 60/423,645, filed on Nov. 4, 2002, provisional application No. 60/600,496, filed on Aug. 10, 2004, provisional application No. 60/618,346, filed on Oct. 12, 2004.

(51) Int. Cl.
*A61M 35/00* (2006.01)
*A61M 1/00* (2006.01)

(52) U.S. Cl. .................. 604/541; 604/290; 604/540

(58) Field of Classification Search ................ 604/317, 604/290, 540
See application file for complete search history.

(56) References Cited

U.S. PATENT DOCUMENTS

| 3,066,672 | A | * | 12/1962 | Crosby, Jr. et al. | ........ 600/573 |
| 3,144,868 | A |   | 8/1964  | Jascalevich |  |
| 3,860,000 | A |   | 1/1975  | Wootten et al. |  |
| 3,884,808 | A |   | 5/1975  | Scott |  |
| 3,924,625 | A |   | 12/1975 | Peterson |  |
| 4,082,095 | A | * | 4/1978  | Mendelson et al. | ........ 604/38 |
| 4,116,589 | A |   | 9/1978  | Rishton |  |
| 4,315,509 | A |   | 2/1982  | Smit |  |
| 4,344,435 | A |   | 8/1982  | Aubin |  |
| 4,356,824 | A |   | 11/1982 | Vazquez |  |
| 4,381,765 | A | * | 5/1983  | Burton | ........ 600/32 |

(Continued)

FOREIGN PATENT DOCUMENTS

EP  1 374 930 A1  1/2004

(Continued)

OTHER PUBLICATIONS

Shapiro, Kenneth J., "Animal Models of Human Psychology." Seattle: Hogrefe & Huber, 1998, pp. 111-211.*

(Continued)

*Primary Examiner*—Melanie J Hand
(74) *Attorney, Agent, or Firm*—Proskauer

(57) ABSTRACT

To treat obesity, a tube is positioned that passes through a patient's abdominal wall into the upper digestive system of the patient. The patient is allowed to carry out his/her everyday affairs including ingesting food. After the patient has ingested food, the food is extracted by pumping it out of the upper digestive system through the tube. This approach is less invasive than current surgical procedures for reducing weight and allows patients to live a normal and active lifestyle without experiencing adverse side effects.

54 Claims, 15 Drawing Sheets

U.S. PATENT DOCUMENTS

| | | | | |
|---|---|---|---|---|
| 4,393,873 | A | | 7/1983 | Nawash et al. |
| 4,449,972 | A | * | 5/1984 | Kruger .................. 604/103.11 |
| 4,525,156 | A | * | 6/1985 | Benusa et al. .................. 604/28 |
| 4,553,960 | A | | 11/1985 | Lazarus et al. |
| 4,642,092 | A | | 2/1987 | Moss |
| 4,723,547 | A | | 2/1988 | Kullas et al. |
| 4,822,338 | A | | 4/1989 | Longmore |
| 4,834,724 | A | | 5/1989 | Geiss |
| 4,899,747 | A | | 2/1990 | Garren et al. |
| 5,071,405 | A | | 12/1991 | Piontek et al. |
| 5,234,454 | A | | 8/1993 | Bangs |
| 5,259,399 | A | | 11/1993 | Brown |
| 5,306,300 | A | | 4/1994 | Berry |
| 5,411,022 | A | | 5/1995 | McCue et al. |
| 5,520,634 | A | | 5/1996 | Fox et al. |
| 5,520,662 | A | | 5/1996 | Moss |
| 5,601,604 | A | | 2/1997 | Vincent |
| 5,618,296 | A | | 4/1997 | Sorensen et al. |
| 5,741,287 | A | | 4/1998 | Alden et al. |
| 5,868,141 | A | | 2/1999 | Ellias |
| 5,972,399 | A | * | 10/1999 | Lapre et al. .................. 426/302 |
| 5,989,231 | A | * | 11/1999 | Snow et al. .................. 604/264 |
| 6,039,251 | A | | 3/2000 | Holowko et al. |
| 6,077,243 | A | * | 6/2000 | Quinn .................. 604/93.01 |
| 6,077,250 | A | | 6/2000 | Snow et al. |
| 6,210,347 | B1 | | 4/2001 | Forsell |
| 6,322,495 | B1 | * | 11/2001 | Snow et al. .................. 600/114 |
| 6,381,495 | B1 | | 4/2002 | Jenkins |
| 6,447,472 | B1 | | 9/2002 | Moss |
| 6,453,907 | B1 | | 9/2002 | Forsell |
| 6,454,785 | B2 | | 9/2002 | De Hoyos Garza |
| 6,506,179 | B1 | | 1/2003 | Tiefenthal et al. |
| 6,511,490 | B2 | | 1/2003 | Robert |
| 6,533,734 | B1 | * | 3/2003 | Corley et al. .................. 600/573 |
| 6,579,301 | B1 | | 6/2003 | Bales et al. |
| 6,615,084 | B1 | | 9/2003 | Cigaina |
| 6,627,206 | B2 | | 9/2003 | Lloyd |
| 6,659,974 | B1 | | 12/2003 | Moss |
| 6,752,790 | B2 | | 6/2004 | Coombs |
| 6,755,869 | B2 | | 6/2004 | Geitz |
| 2001/0049490 | A1 | | 12/2001 | Slanda |
| 2003/0069553 | A1 | | 4/2003 | Talamonti |
| 2003/0109935 | A1 | * | 6/2003 | Geitz .................. 623/23.65 |
| 2003/0208113 | A1 | * | 11/2003 | Mault et al. .................. 600/316 |
| 2003/0225369 | A1 | | 12/2003 | McMichael |

FOREIGN PATENT DOCUMENTS

| | | |
|---|---|---|
| JP | 62-224358 | 10/1987 |
| JP | 3-18378 | 1/1991 |
| JP | 200129434 | 2/2001 |
| WO | WO 94/15655 | 7/1994 |
| WO | WO 99/25418 | 5/1999 |
| WO | WO 01/68007 A1 | 9/2001 |

OTHER PUBLICATIONS

Cantor, David. Shapiro, Kenneth J., "Animal Models of Human Psychology." Animals' Agenda. 18.3, p. 36, p. 1.*

Herman, Lawrence L. et al, "Percutaneous endoscopic gastrostomy for decompression of the stomach and small bowel", Gastrointestinal Endoscopy, 38:3, pp. 314-318.*

Suazo-Barahona, Jorge et al, "Obesity: A Risk Factor for Severe Acute Biliary and Alcoholic Pancreatitis", Am. J. Gastroenterology, 93:8, pp. 1324-1328.*

Harper, P.H. et al, "The Long-term Outcome in Crohn's Disease", Am. Soc. Gastrointestinal Endoscopy, 30:3, pp. 174-179.*

Michaud, Laurent et al, "Gastrostomy as a Decompression Technique in Children with Chronic Gastrointestinal Obstruction", J. Ped. Gastroenterology & Nutritiion, 32:82-85, 2001.*

Pearce, C.B. et al, The 'cut and push' method of percutaneous endoscopic gastrostomy tube removal Clinical Nutrition, vol. 19, Issue 2, pp. 133-135, 2000 Copy can be accessed at: http://www.sciencedirect.com/science?_ob=ArticleURL&_udi=B6WCM-45FCHCN-1S&_user=2502287&_rdoc=1&_fmt=&_orig=search&_sort=d&view=c&_acct=C000055109&_version=1&_urlVersio.*

Moshe Shike, MD et al., An Active Esophageal Prosthesis, Gastrointestinal Endoscopy Jan. 1995 vol. 41 No. 1.

Lawerence L. Herman, MD et al., Percutaneous endoscopic gastrostomy for decompression of the stomach and small bowel, Gastronintestinal Endoscopy, 1992 pp. 314-318.

Joshau Felsher,M.D et al., Decompressive percutaneous endoscopic gastrotomy in nonmalignant disease, The American Journal of Surgery 187 (2004) 254-256.

Henry Buchwald, MD et al., Bariatric Surgery, a Systematic Review and Meta-Analysis, JAMA, Oct. 13, 2004-vol. 292, No. 14.

Meissner K. Hepatogastroenterology. Mar.-Apr. 2004;51(56):462-4. Ajuvant surgical decompression gastrostomy: audit of a procedure coming of age.

Michaud L et al., J Pediatr Gastroenterol Nutr. Jan. 2001; 32(1):82-5, Gastrostomy as a decompression technique in children with chronic gastrointestinal obstruction.

Herman LL et al., Gastrointest Endosc. May-Jun. 1992; 38 (3): 314-8, Percutaneous endoscopic gastrostomy for decompression of the stomach and small bowel.

Shike M., Oncology (Huntingt). Jan. 1995:9(1):39-44; discussion 44, Percutaneous endoscopic stomas for enteral feeding and drainage.

Shike M et al., JPEN J Parenter Enteral Nutr. Nov.-Dec. 1989;13(6):648-50. Skin-level gastrostomies and jejunostomies for long-term enter feeding.

Nassif AC. Obes Surg. Mar. 1991;1(1):99-102., Efficient Decompression and Immediate Enteral Hyperaliment via Gastrostomy as an Adjunct to Gastroplasty.

Shike M, Gastrointest Endosc. May-Jun. 1990:36(3):290-2. Combined gastric dranage and jejunal feeding through a percutaneous endoscopic stoma.

Moseh Shike, MD et al. External biliary duodenal drainage through a percutaneous endoscopic duodensotomy, Gastrointestinal Endoscopy, vol. 35, No. 2, 1989.

Moshe Shike, MD et al., Percutaneous endoscopic gastrostomy and jejunostomy for long-term feeding in patients with cancer of the head and neck, otolaryngology Head and Neck Surgery vol. 101 (5), 1989.

T. Lorentzen et al., Percutaneous Gastrostomy guided by Ultrasound and Fluoroscopy ACTA Radiologica 36 (1995) 159-162.

Francesco Doenz et al., Versatility of the Proximal Cope Loop Catheter, American Journal of Roentgenolog Jan. 1989, 205.

K.E. Gehman et al. Percutaneous Gastrojejunostomy with a Modified Cope Loop Catheter, American Journal of Roentgenology 155.79-80 (1990).

Robin R. Gray, MD, et al., Modified Catheter for Percutaneous Gastrojejunostomy Radiology 1989; 173:276-278.

Richard Duszak, Jr. MD, Percutaneous Gastrostomy and Jejunostomy http.//www.emedicine.com/radio/topic798.htm (Jul. 8, 2005).

Katherine M. Flegal, PhD et al. Prevalence and Trends in Obesity Among US Adults, 1999-2000 JAMA, Oct. 9, 2002 vol. 288, No. 14, 1723-1727.

Andrew Luck and Peter Hewett Lapraoscopic Gastrostomy: Towards The Ideal Technique Aust. N.Z. J. Surg. (1998) 68,281-283.

F.J. Thornton et al., Percutaneous Radiologic Gastrostomy With and Without T-Fastener Gastropexy: A Randomized Comparison Study CardioVascular Interventional Radiology (2002) 25:467-471.

Ozmen et al. Percutaneous Radiologic Gastrostomy, European Journal of Radiology 43 (2002) 186-195.

Goldstein DJ., Beneficial health effects of modest weight loss, Int J Obes 1992 16:397-415.

* cited by examiner

METHOD FOR TREATING OBESITY BY EXTRACTING FOOD

RELATED APPLICATIONS

This application is a continuation-in-part application of U.S. patent application Ser. No. 10/702,194, filed Nov. 4, 2003, now abandoned which claims the benefit of U.S. Provisional Application No. 60/423,645, filed Nov. 4, 2002, each of which is incorporated by reference herein. This application claims priority to U.S. Provisional Application No. 60/600,496, filed Aug. 10, 2004 and U.S. Provisional Application No. 60/618,346, filed Oct. 12, 2004, each of which is incorporated by reference herein.

BACKGROUND OF THE INVENTION

Obesity is a major health problem in the United States and other countries. The National Health and Nutrition Examination Survey (1988-1994) reported that approximately 20-25% of Americans are obese, while another study estimated the percentage of overweight Americans to be between 60% and 65% (Flegal K M, Carroll M D, Ogden C L, Johnson C L "Prevalence and trends in obesity among US adults, 1999-2000" JAMA 2002; 288:1723-1727). Obesity can cause numerous health problems, including diabetes, degenerative joint disease, hypertension, and heart disease. Weight reduction can be achieved by increased caloric expenditure through exercise and/or by reduced caloric consumption through diet. However, in most cases, weight gain often recurs and improvements in related co-morbidities are often not sustained.

Surgical procedures present an increasingly common solution for obese patients. Surgical procedures include, for example, stapled gastroplasty, banded gastroplasty, gastric banding, gastric bypass surgery, and bilopancreatic bypass. However, these surgical procedures are invasive, risky and expensive to perform, and many patients regain a substantial portion of the lost weight.

SUMMARY OF THE INVENTION

The present invention is directed to apparatuses and methods for treating obesity or facilitating weight loss. A passageway is introduced into a patient's upper digestive system such that it passes through the patient's abdominal wall. The patient is allowed to carry out his/her everyday affairs including ingesting food. After the patient has ingested food, the food is extracted by pumping it out of the upper digestive system through the passageway. This approach is less invasive than the procedures discussed above, easy to perform, easy to reverse and has successfully resulted in significant weight loss in obese patients.

DETAILED DESCRIPTION OF PREFERRED EMBODIMENTS

As used herein, the term "food" includes both solid and liquid substances that have been ingested by the patient, the term "ingest" or "ingested" includes eating and drinking, and the term "upper digestive system" includes the stomach 3, duodenum 4 and proximal jejunum of the patient.

Figure 1:
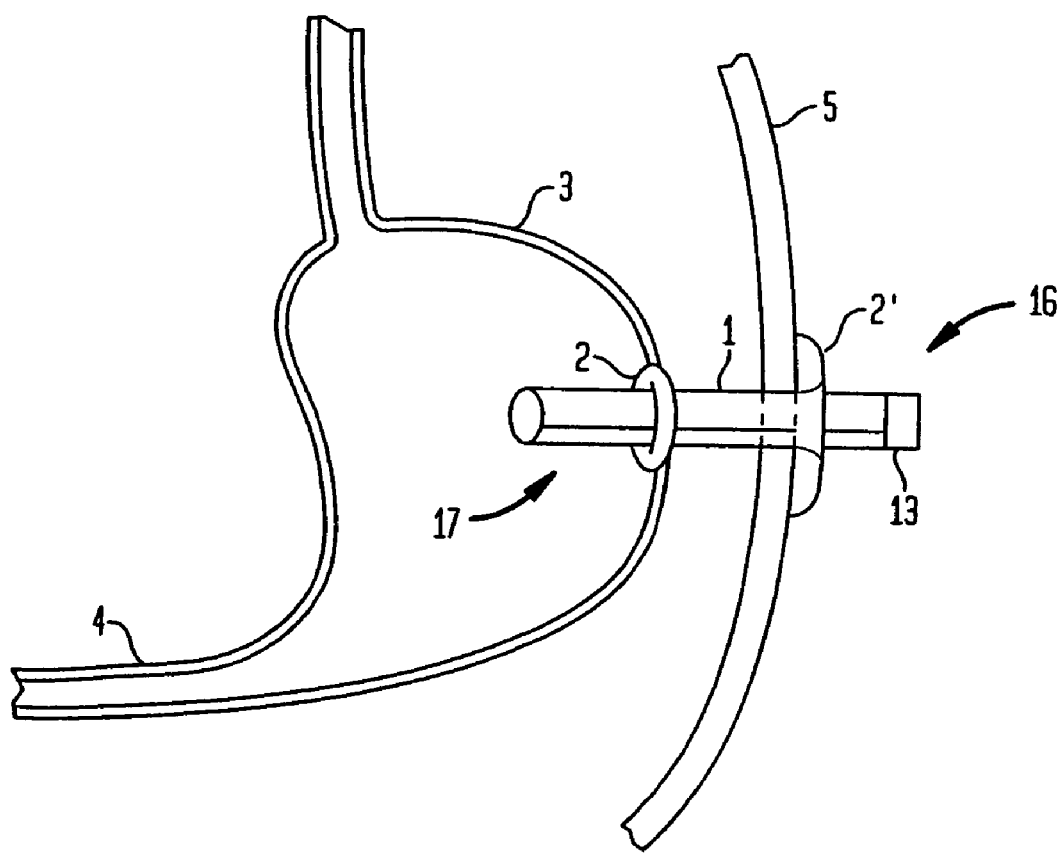
FIG. 1 is a schematic view of a first embodiment of the present invention installed in a patient.

In a first embodiment of the present invention as shown in FIG. 1, a transabdominal tube 1 is placed through a patient's abdominal wall such that a distal end portion 17 of the tube 1 is disposed inside the stomach 3 of the patient and a proximal end portion 16 of the tube 1 extends out from the skin 5 of the patient. The tube 1 preferably has a diameter that is 20 to 36 French in size (1 French=⅓ mm). Most preferably, the diameter is greater than 28 French and the tube resists collapsing when extraction is performed. Optionally, the tube 1 may be stiffened, made durable and less collapsible by, for example, braiding the tube using nylon. Alternatively, the tube may be wrapped with wire material. Suitable materials for the tube 1 include polyurethane, silicone and other similar materials. The tube 1 may be opaque.

A retention member is attached to the tube 1 to prevent the tube 1 from falling out of the patient. In one embodiment, the retention member is inflatable such as the inflation portion 2 (balloon anchor) shown in FIG. 1. As shown in FIG. 1, the inflation portion 2 is provided at the distal end portion 17 of the tube 1 to prevent the tube 1 from coming out of the stomach 3. FIG. 1 also illustrates a non-inflatable retention member flange 2' at the proximal end portion 16 of the tube 1 to prevent the tube 1 from falling into the patient's upper digestive system. A cap 13 is detachably provided at the end of the proximal end portion 16 and seals the tube 1 when it is attached. The cap 13 is removed when a pump 8, 9 (shown in FIGS. 2 and 3, respectively) is attached to the tube 1 to remove food from the upper digestive system of the patient.

Reference is now made to methods which may be used to insert the tube 1. These methods entail less risk of complications and less cost than conventional, surgical methods of treating obesity, and patients who undergo these treatments are typically discharged the same day of the operation. These methods are therefore especially advantageous for use in treating obese patients because such patients are at increased risk for surgical complications due to their obesity.

The tube 1 may be inserted, for example, through a procedure similar to insertion of feeding tubes by Percutaneous Endoscopic Gastrostomy (PEG). A variety of methods of performing PEG are well known in the art, and any one of the methods may be used to insert the tube 1. PEG procedures have been successfully completed in over 90 percent of attempts. PEG may be performed under conscious sedation induced by, for example, meperidine and midazolam. According to one method of PEG known as the pull method, an endoscope is inserted into the stomach through the mouth of the patient. The stomach is insufflated by blowing air into the stomach through the endoscope. The insufflation brings the stomach in apposition to the abdominal wall and allows for direct access from the skin to the stomach of the patient.

An insertion site is located by surveying the interior of the stomach with the endoscope. The endoscope is then used to illuminate the selected insertion site in such a way that the light of the endoscope is visible from outside of the patient's body through the skin of the patient.

An incision is made at the place on the patient's skin indicated by the light from the endoscope and at the corresponding location on the exterior wall of the stomach. A cannula is then inserted through the incision and a guide wire is inserted into the stomach through the cannula. Graspers on the end of the endoscope grab hold of the distal portion of the guide wire in the stomach and the endoscope is withdrawn from the patient while the graspers hold the guide wire. The guide wire is of sufficient length to allow a proximal portion of it to extend out of the patient from the cannula after the distal portion is withdrawn from the stomach and through the patient's mouth by the endoscope.

The end of the guide wire extending out from the patient's mouth is attached to the proximal end of the tube 1, which is drawn though the mouth and esophagus and into the stomach of the patient by pulling on the proximal end of the guide wire. The tube 1 is then pulled through the incision in the stomach and skin of the patient until only the distal end portion 17 and the inflation portion 2 of the tube 1 remain inside of the stomach. Optionally, the tube 1 may have a coned tip to help move the tube 1 through the incision in the stomach. Optionally, a wire at the tip of the cone may be used for pulling the tube 1 through the incision. Once the tube 1 is in place, the coned tip may be cut off. The cannula is removed as the proximal end 16 of the tube 1 is drawn through the incision in the stomach, and is removed entirely when the proximal end 16 of the tube 1 is disposed at the patient's skin. The inflation portion 2 of the tube 1 is then inflated by introducing fluid into the inflation portion 2 through the inflation lumen 26. The inflated inflation portion holds the tube 1 in place and the guide wire is removed from the tube 1. A non-inflatable retention member such as a flange 2' may be placed on the proximal end portion 16 of the tube 1 to keep the tube 1 disposed at the patient's skin.

An alternate method of PEG known as push PEG may also be used to insert the tube 1. The tube 1 is pushed through the incision in the stomach and the skin of the patient until it is disposed as described hereinabove with respect to the pull method.

A third method which may be used for inserting the tube 1 via PEG is known as the Russell method. As with both the push method and the pull method, the insertion site is located via endoscopy. An incision is made in the skin and stomach and a guide wire is inserted through the incision into the stomach via a cannula or needle. A dilator (or introducer) with a peel away sheath is guided along the guide wire and inserted into the stomach. After the dilator (introducer) and sheath are inside the gastric lumen, the dilator is removed and the tube 1 is inserted along the guide wire and through the peel away sheath. The sheath is then peeled away and the tube 1 is fixed in place.

The tube 1 may also be inserted without using an endoscope, for example, through a procedure similar to insertion of feeding tubes by Percutaneous Radiological Gastrostomy (PRG). According to PRG, the stomach is insufflated via a nasogastric tube. Organs which may be interposed between the stomach and the abdominal wall, such as the colon, are excluded by CT scan or ultrasonography. Exclusion of interposed organs may also be accomplished after insufflation by fluoroscopy. The selection of the insertion site is also determined by fluoroscopy or a similar method.

After the insertion site has been located, the tube 1 may be inserted transabdominally as in the Russell method of PEG. Alternatively, a guide wire may be inserted as in the endoscopic pull method. The wire is then maneuvered through the stomach and esophagus and out of the patient's mouth and is used to guide the tube 1 back through the mouth, esophagus and stomach and out of the insertion site (see, e.g., Mustafa N. Zmen et al. "Percutaneous Radiologic Gastrostomy" European Journal of Radiology 43:186-95).

The tube 1 may be inserted surgically. One suitable surgical technique that may be used to insert the tube 1 is the laparoscopic method. In this method, after pneumoperitoneum has been created, a 5 mm trocar is used to grasp a site on the anterior stomach wall that is appropriate for tube placement without excessive tension on the stomach. A skin incision down to the rectus sheath is made. A trocar is placed through the rectus sheath and the stomach wall is grasped and pulled upwards. An incision is made in the stomach and the tube 1 is inserted. Using the retention member at the distal end portion 17 of the tube 1, the stomach is brought snugly against the abdominal wall. The tissue is sutured around the tube 1. (see, e.g., Andrew Luck et al. "Laparoscopic Gastrostomy: Towards the Ideal Technique" Aust. N. Z. J. Surg. (1998) 68:281-283).

The tube 1 may be inserted in other portions of the upper digestive system besides the stomach. For example, direct jejunostomy, wherein a tube is inserted transabdominally into the jejunum, may be accomplished through methods similar to those described hereinabove with reference to gastrostomy tube placement. The retention member of the device should generally be smaller for jejunostomy procedures to avoid irritation of the jejunum or obstruction of the jejunal lumen.

Figure 1A:
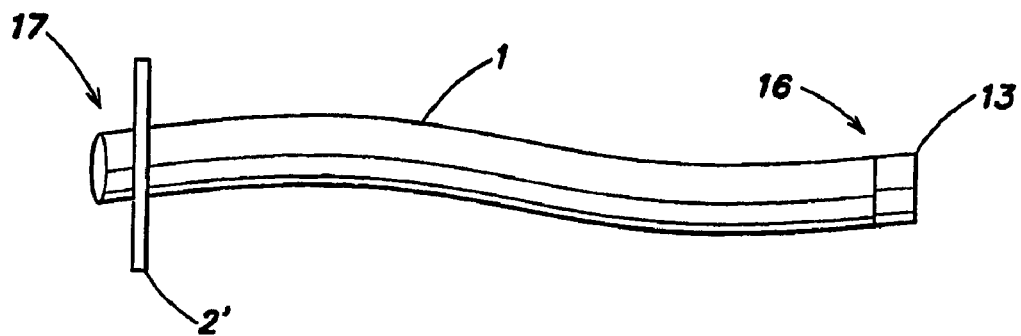
FIG. 1A is a schematic view of a tube.
Figure 1B:
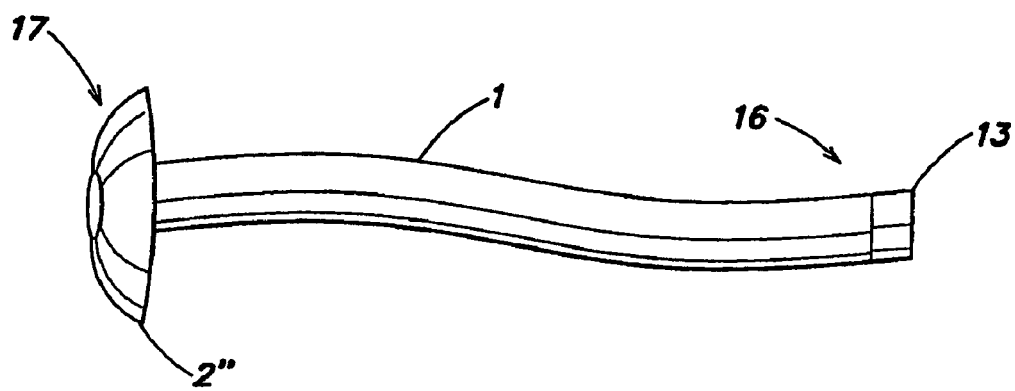
FIG. 1B is an alternate view of a tube.

FIG. 1 illustrates an inflatable retention member, i.e. the inflation portion 2, that is attached to the tube 1 to prevent the tube 1 from falling out of the patient. FIGS. 1, 1A and 1B illustrate two alternative non-inflatable retention members that may be used in place of and/or in addition to the inflatable portion 2. FIGS. 1 and 1A illustrate a flange 2' and FIG. 1B illustrates a dome 2". A flange 2' or dome 2" that is located at the distal end portion 17 of the tube 1 helps to prevent the tube 1 from coming out of the stomach 3 or other section of the upper digestive system. A flange 2' or dome 2" that is located at the proximal end portion 16 of the tube 1 helps to prevent the tube from falling into the patient's upper digestive system.

Figure 1C:
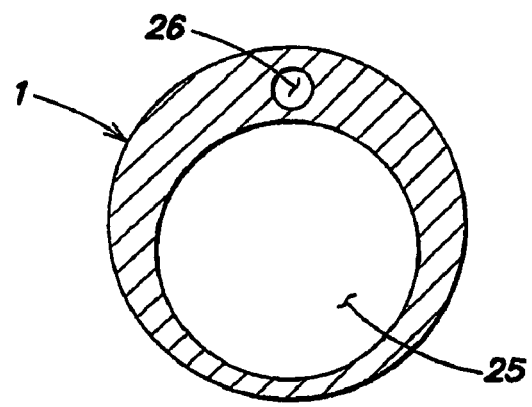
FIG. 1C is a cross sectional schematic view of a tube.
Figure 7:
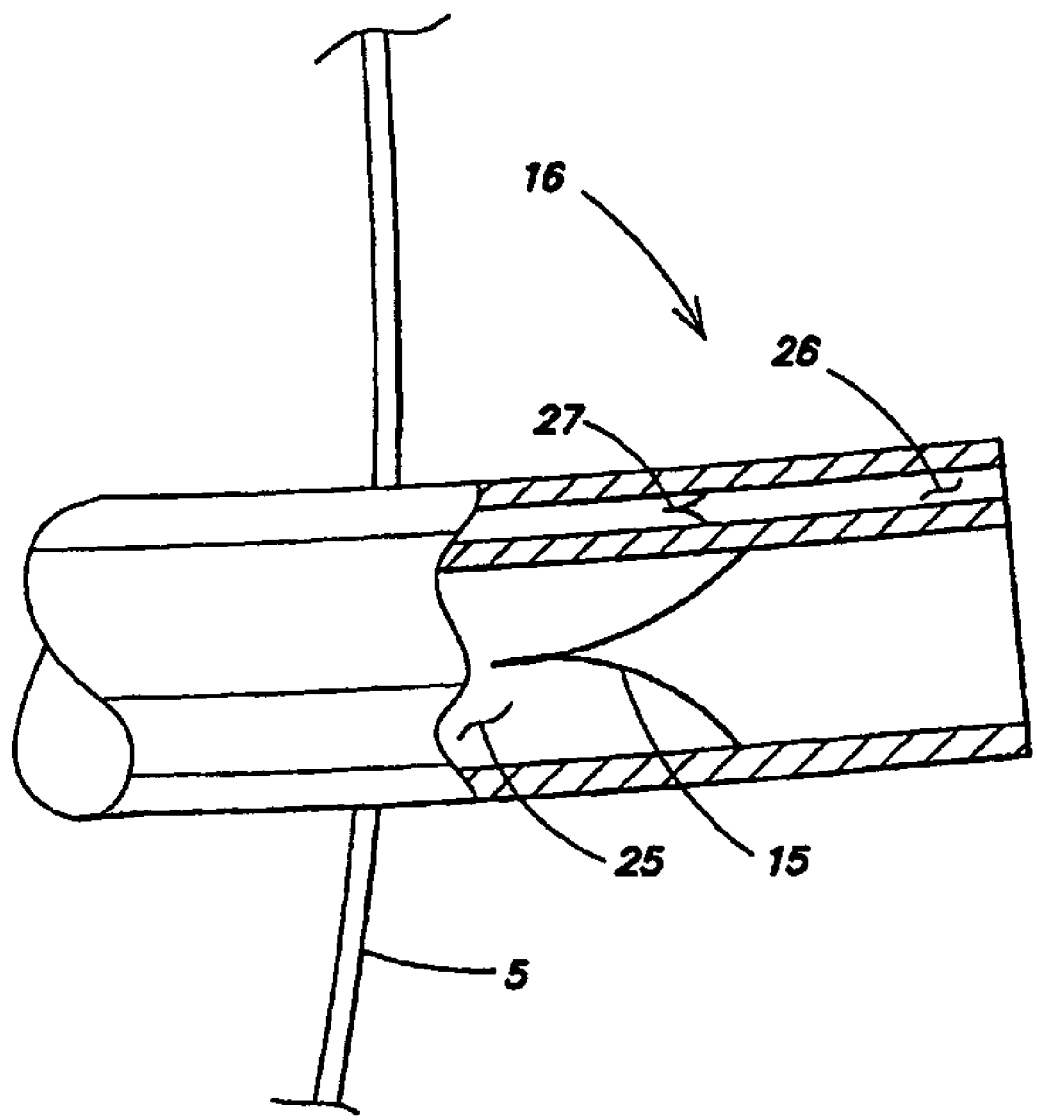
FIG. 7 is an axial cross sectional schematic view showing valves provided in the lumens of a tube in an embodiment of the present invention.

When an inflatable retention member is used, the tube 1 preferably has an inflation lumen 26 so that the inflatable retention member can be inflated. FIG. 1C shows a cross section of the tube 1 taken perpendicular to the axis of tube 1. Inflation lumen 26 extends from the inflation portion 2 to the proximal end portion 16 of the tube 1 and is a pathway for introducing fluid, such as water or air, to the inflation portion 2 from outside of the patient. Removal lumen 25 extends from the proximal end portion 16 to the distal end portion 17 of the tube 1 and is a pathway for the removal of food from the stomach 3 or other part of the upper digestive system of the patient. The inflation lumen 26 is preferably minimal in size to allow the removal lumen 25 to be as wide as possible within the tube 1. In the illustrated embodiment, valves 15, 27 are provided in lumens 25, 26, respectively, as shown in FIG. 7. With the non-inflatable retention members 2' and 2" shown in FIGS. 1A and 1B, the second lumen 26 in tube 1 can be eliminated.

Inflatable retention members are suitable for use with procedures similar to the push method, while either inflatable or rigid retention members are suitable for use with procedures similar to the pull method. One example of a tube that has an inflatable retention member is taught in Tiefenthal et al. (U.S. Pat. No. 6,506,179), the entire contents of which are incorporated herein by reference. An alternative deformable retention member is taught in Snow et al. (U.S. Pat. No. 6,077,250), the entire contents of which are incorporated herein by reference.

Retention members that may be deformed in situ allow the tube 1 to be removed without additional endoscopy. The retention member is deflated or deformed and the tube 1 is pulled out using traction. In cases where the retention member is rigid, the tube 1 may be cut close to the skin and removed endoscopically.

It is preferable for the stomach to be positioned up against the inner abdominal wall. This may be accomplished by insufflation during the tube placement procedure and after the tube 1 has been placed due to the retention member. For example, as shown in FIG. 1, retention members at the proximal end portion 16 and distal end portion 17 of the tube 1 anchor the stomach up against the abdominal wall. The stomach may also be anchored to the abdominal wall by gastropexy, which may prevent complications arising from tube placement and may facilitate the placement procedure. In addition, jejunopexy is important in jejunostomy procedures in order to secure the jejunum during the tube placement procedure (see Zmen et al., supra). For example, to secure the stomach or jejunum to the abdominal wall, T-shaped metal or nylon fixing members may be inserted trans-gastrically or trans-jejunally close to the tube insertion site. The fixing members assume a T shape after insertion and are tied near to the skin. Four fixing members are typically disposed in a square pattern around the tube insertion site to secure the stomach or jejunum. (see, e.g., F. J. Thornton et al. "Percutaneous Radiologic Gastrostomy with and without T-Fastener Gastropexy: a Randomized Comparison Study" Cardiovasc Intervent Radiol. 2002 November-December; 25(6):467-71).

Figure 2:
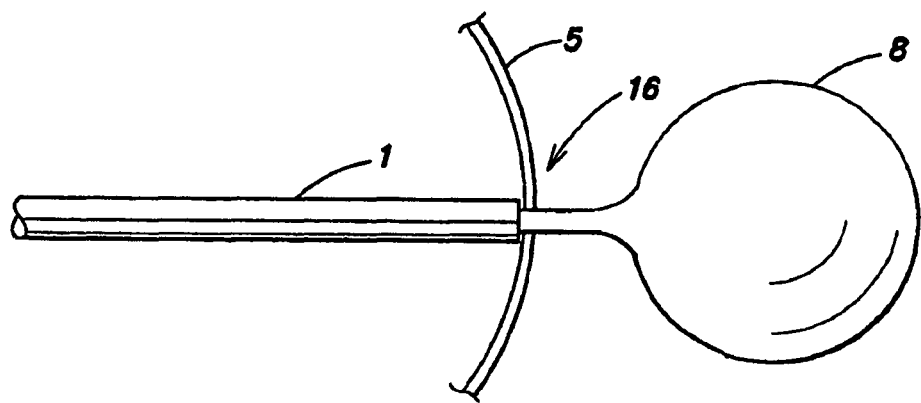
FIG. 2 is a schematic view of a variation of an embodiment of the present invention that uses a manual bulb pump.
Figure 3:
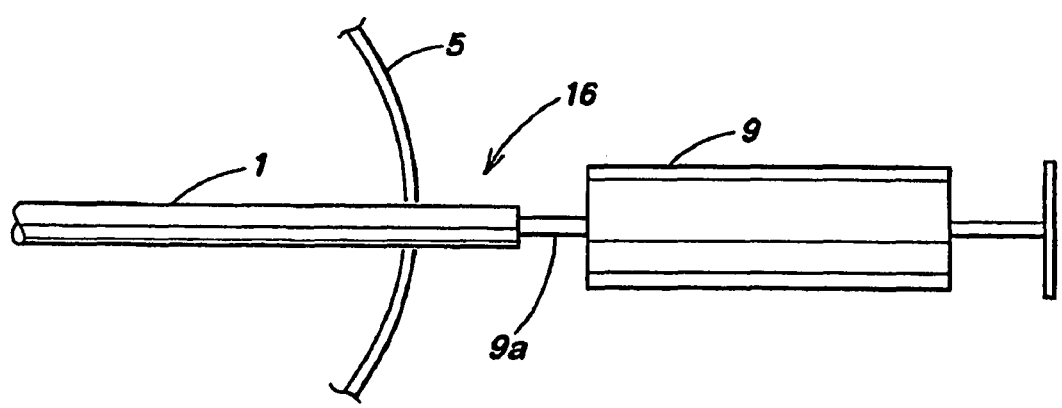
FIG. 3 is a schematic view of a variation of an embodiment of the present invention that uses a syringe as a pump.

Reference is now made to various forms of pumps which are attachable to the proximal end portion 16 of the tube 1. Any conventional pump, the construction of which will be readily understood to one skilled in the art, may be used. FIGS. 2 and 3, for example, display pumps 8 and 9 which are attachable to the proximal end portion 16 of the tube 1 for removal of food from the stomach 3 or upper digestive system of the patient. It would be suitable to use a pump that extracts more than 750 ml of food from the upper digestive system of a patient within 30 minutes or less. The pump may be operated intermittently to prevent tube collapse, tube clogging or mucosal irritation. The pump may be manual or battery operated. Optionally, a rechargeable power supply may be incorporated into the pump, and the pump may be configured to be carried on a patient's belt.

FIG. 2 depicts a manual bulb pump 8 that is attached to the proximal end portion 16 of the tube 1 and is operated to remove food from the patient's upper digestive system through the tube 1. The manual bulb pump 8 preferably comprises silicone rubber or a similar flexible material so as to permit the contents of the bulb pump 8 to be evacuated by squeezing the bulbous end of the bulb pump 8. The circumference of a tapered end essentially corresponds to an interior circumference of the lumen 25 of the tube 1. To operate the manual bulb pump 8, air is first evacuated from the bulb pump 8 by squeezing the bulb, and then the tapered end of the bulb pump 8 is inserted into the lumen 25 of the proximal end portion 16 of the tube 1 so as to create a seal between the tapered end and the tube 1. The bulb is then released to allow it to re-inflate. The negative pressure in the bulb pump 8 (when it is released) causes food to flow out from the upper digestive system toward the proximal end portion 16 of the tube 1 and into the bulb of the manual bulb pump 8. The bulb pump 8 is then disengaged from the tube 1 and the removed food is evacuated from the bulb. The cycle may be repeated until a desired amount of food is removed from the upper digestive system of the patient.

FIG. 3 depicts another pumping arrangement in which a pump in the form of a syringe 9 is attached to the proximal end portion 16 of the tube 1 and is operated to remove food from the patient's upper digestive system through the tube 1. The syringe 9 preferably comprises a tapered end portion with an aperture at the distal end thereof. The circumference of the tapered end portion 9a corresponds to the interior circumference of the lumen 25 of the tube 1. To operate the syringe 9 to remove food from the upper digestive system of the patient, the contents (air or food) of the syringe 9 are evacuated by depressing the plunger. The tapered end portion 9a of the syringe 9 is inserted into the proximal end portion 16 of the tube 1 so as to create a seal between the tapered end portion 9a and the tube 1. The plunger of the syringe 9 is then withdrawn so as to create negative pressure to draw food out from the upper digestive system through the tube 1 and into the syringe 9. The syringe 9 is then disengaged from the tube 1 and evacuated by, for example, depressing the plunger thereof. 60 cc is an example of a suitable size for the syringe 9. The cycle may be repeated until a desired amount of food is removed from the upper digestive system of the patient.

The manual bulb pump 8 and syringe 9 may be activated by the patient or by a health care provider at a predetermined time after eating. The predetermined time is preferably set by a physician and, for example, may be 20-30 minutes. A physician may also determine a maximum volume of food to be removed from the upper digestive system of the patient after each meal. The maximum volume may be set in terms of a maximum number of pumping cycles which is told to the patient or health care provider if the pump 8, 9 is manually operated.

In a preferred embodiment, the pump that is used to extract food from the patient's upper digestive system periodically reverses direction and pumps air and/or water into the upper digestive system of the patient during the periods of reverse operation. The air and/or water helps to solubilize or breakdown the food in the upper digestive system so that it can be pumped out easily. In addition, the air and/or water helps prevent the tube 1 from being suctioned up against the stomach wall while food is extracted from the upper digestive out through the tube 1. For example, every seven seconds of pumping may be followed by two seconds of reverse operation.

Figure 4:
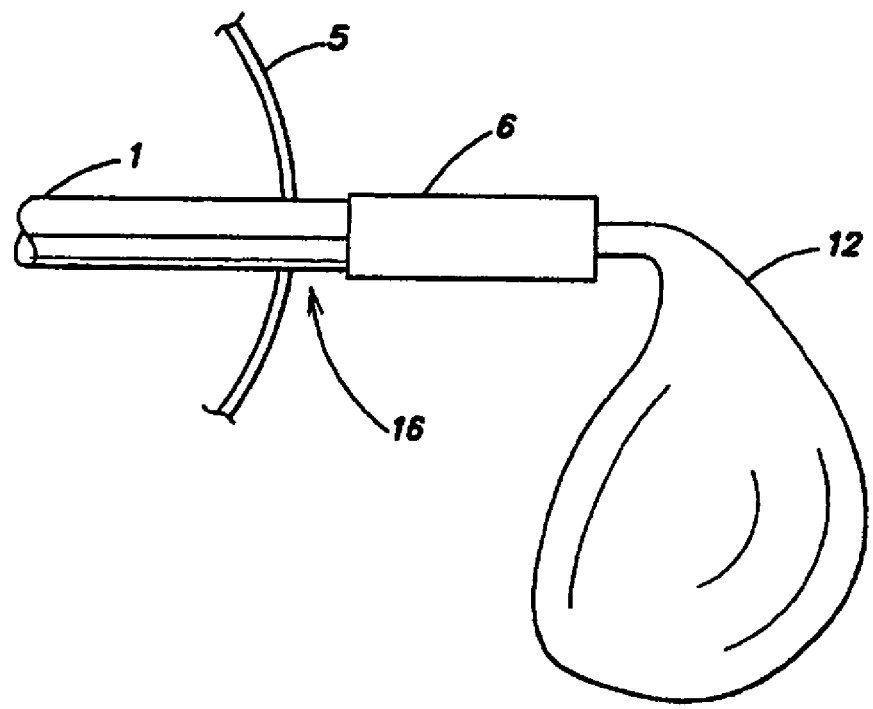
FIG. 4 is a schematic view of a variation of an embodiment of the present invention that uses a bag connected to a pump.
Figure 11:
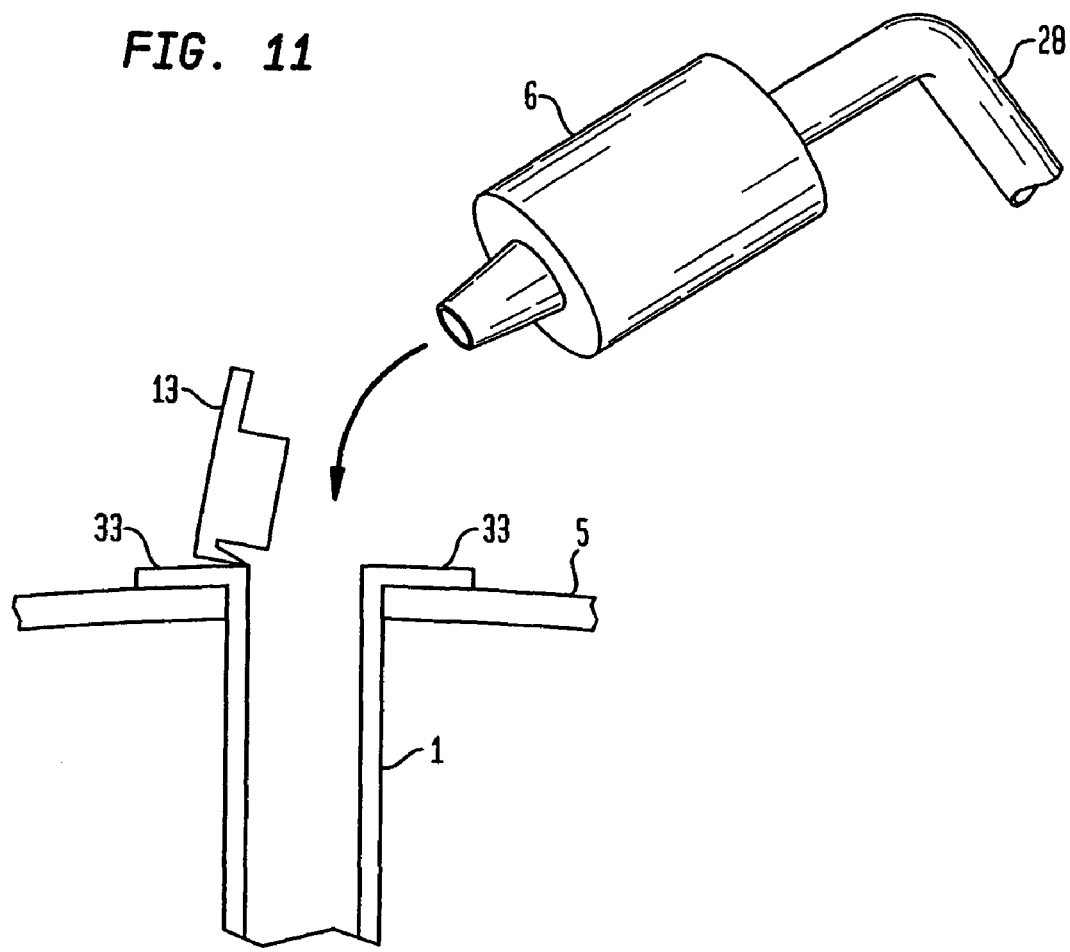
FIG. 11 is a schematic view of the proximal end portion of a tube lying substantially flush with a patient's abdominal wall.
Figure 16:
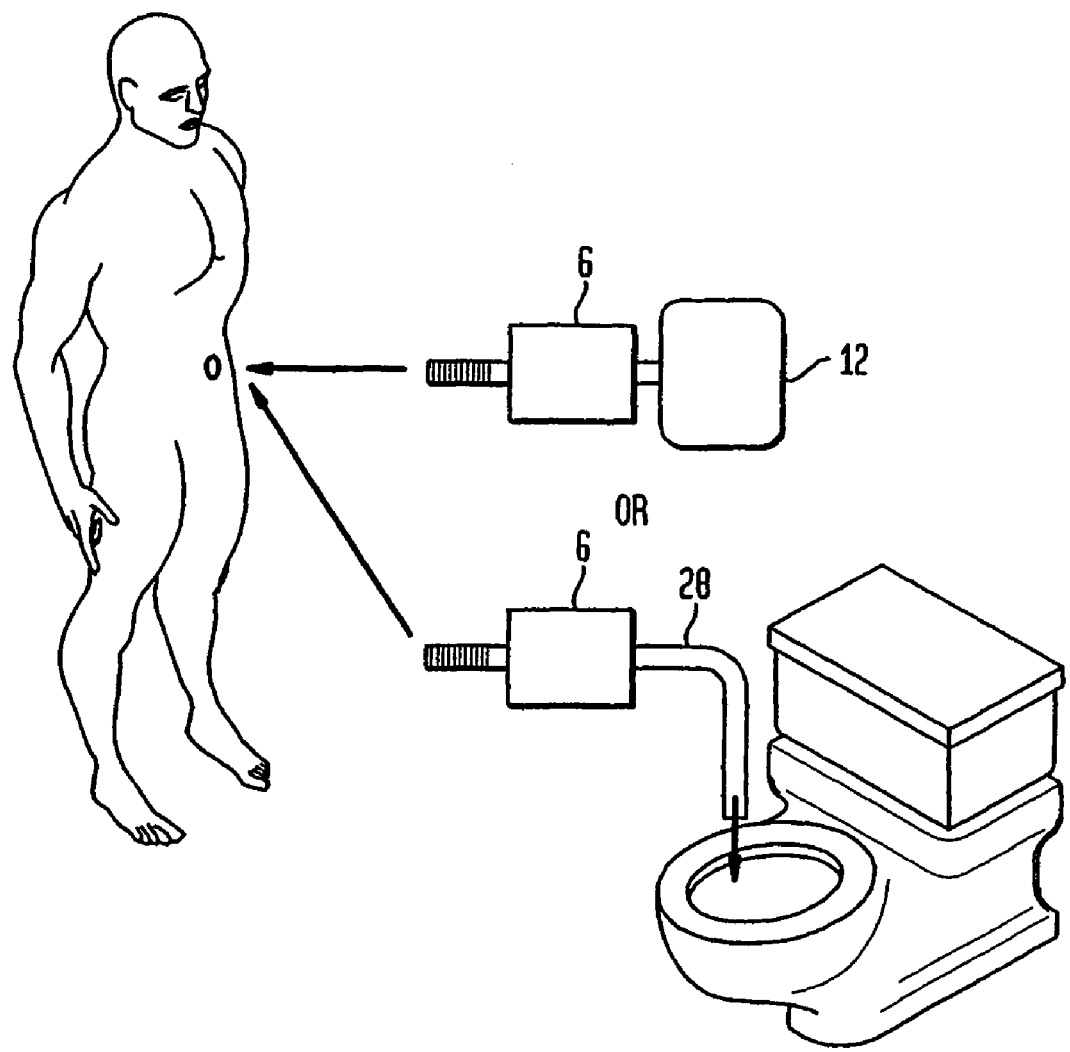
FIG. 16 illustrates how an embodiment of the present invention installed in a patient is used.

FIG. 4 illustrates a variation of an embodiment of the present invention in which the extracted food is evacuated from a pump 6 into a bag 12 that is attached to the pump 6. As shown in FIG. 4, after the food is pumped out of the upper digestive system of the patient by the pump 6, the food may be stored in a bag 12 that is attachable to the proximal end portion of the pump 6. The bag 12 may be opaque, scented, biodegradeable and worn by the patient on a belt or other strap. Alternatively, as shown in FIGS. 11 and 16, the food may be pumped from the patient's upper digestive system into the pump 6 and then into a tube 28 attached to the pump 6. The contents of the tube 28 attached to the pump 6 may be emptied into a toilet. The tube 28 may be opaque, scented, biodegradeable and flushable down the toilet.

Figure 5:
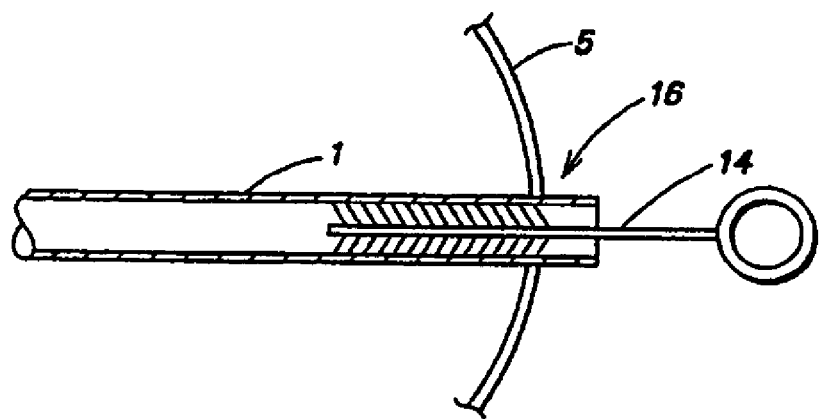
FIG. 5 is a schematic view of how an embodiment of the present invention can be cleaned.

FIG. 5 illustrates a cleaning device being used to clean the tube 1 after food has been extracted from the patient's upper digestive system through the tube 1. As shown in FIG. 5, the tube 1 may be cleaned using a brush 14 that is adapted to clean the inside of the tube 1. The pump 6, manual bulb pump 8 and syringe 9 may be cleaned by flushing them with saline and/or a disinfectant solution after use.

Figure 6:
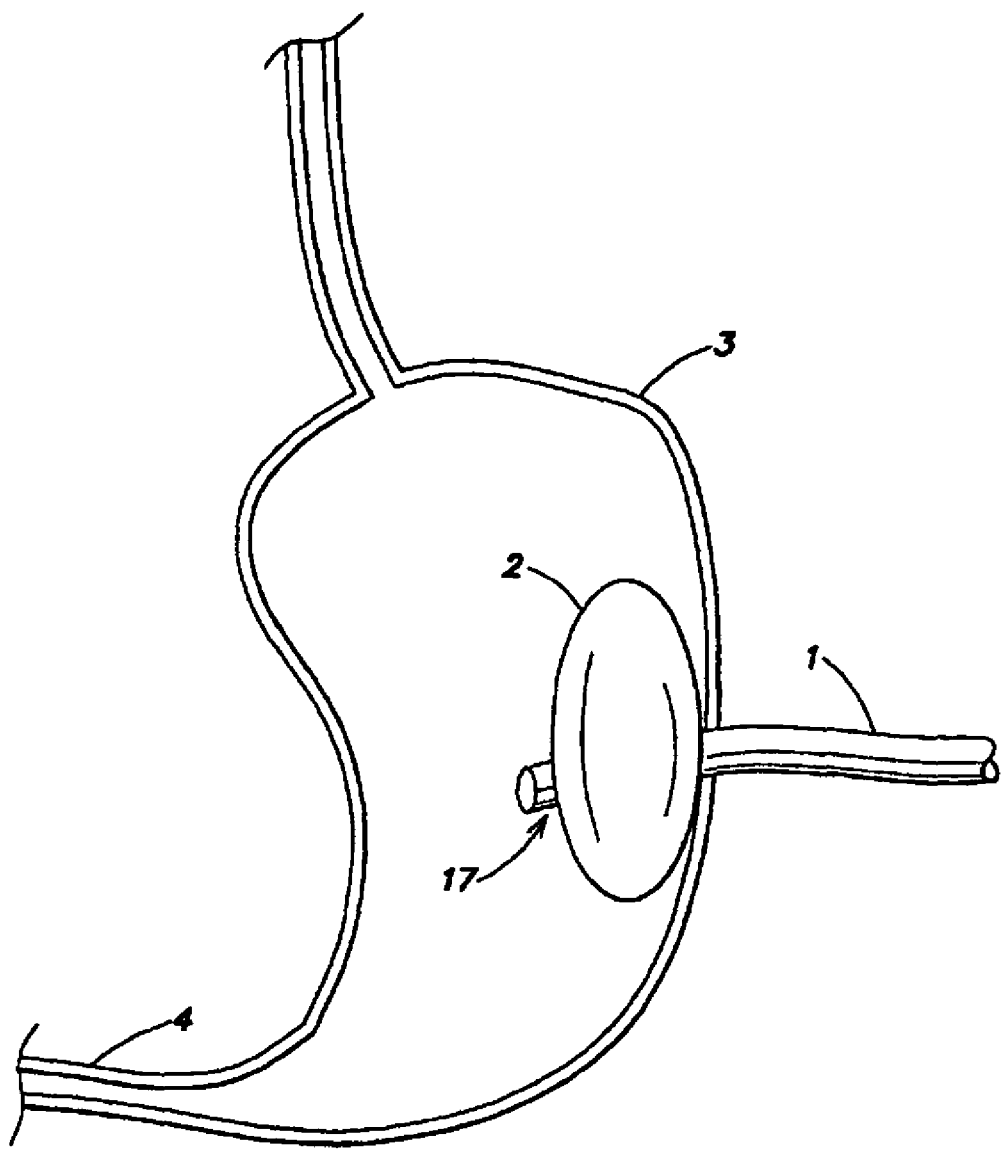
FIG. 6 is a schematic view of a second embodiment of the present invention that uses an inflated balloon anchor.

FIG. 6 illustrates a second embodiment of the present invention in which a feeling of satiety is created in the patient by inflating the balloon anchor. Creating a feeling of satiety curbs the patient's hunger and desire to eat food thereby allowing the patient to eat less and lose weight. As shown in FIG. 6, the inflation portion 2, which is the retention member that holds the tube 1 in the patient's stomach, also serves the function of decreasing stomach capacity to create a feeling of satiety when it is inflated. The inflation portion 2 may be variably inflated by adding or removing fluid through the inflation lumen 26 of the tube 1 (shown in FIG. 1C).

FIG. 7 shows an axial cross sectional view of the tube 1 extending out from the skin 5 of the patient in which the removal lumen 25 and the inflation lumen 26 are visible. In a feature which may be incorporated into any of the various embodiments of the present invention, a valve 15 is provided at the proximal end portion 16 of the tube 1 in the removal lumen 25. The valve 15 ordinarily prevents food from leaving the tube 1. The valve 15 is opened when a pump is attached to the proximal end portion 16 of the tube 1. For example, the tapered end portion of the manual bulb pump 8 (shown in FIG. 2) and the tapered end portion of the syringe 9 (shown in FIG. 3) each push open the valve 15 when they are inserted into the proximal end portion 16 of the tube 1. When the valve 15 is opened by the ends of the pumps, food can be removed as described hereinabove. A cap 13 (shown in FIG. 1) is preferably placed on the proximal end portion 16 of the tube 1 when a pump is not attached. The cap 13 may be pressed onto the end of the tube 1, threaded on the end of the tube 1, or may have projections which are frictionally inserted into the ends of lumens 25, 26 to seal them in a closed condition.

FIG. 7 also shows a valve 27 provided at the proximal end portion 16 of the tube 1 in the inflation lumen 26. The valve 27 prevents the fluid used to inflate the inflation portion 2 from escaping the inflation portion 2 through the inflation lumen 26. That is, the valve 27 prevents the inflation portion 2 from deflating. If it becomes necessary to deflate the inflation portion 2 to remove the tube 1 from the upper digestive system of the patient, or to further inflate the portion 2, a needle on a syringe may be inserted into the inflation portion 26 so as to open the valve 27 by pushing the needle through the valve members. The fluid used to inflate the inflation portion 2 may then be removed or added with the syringe.

Figure 8:
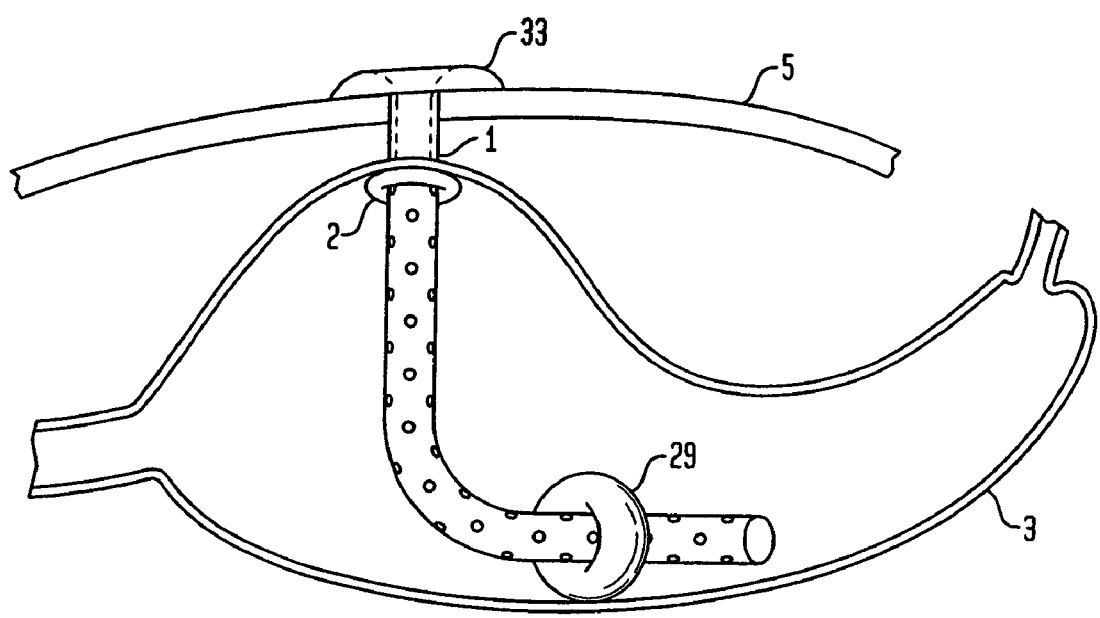
FIG. 8 is a schematic view of a third embodiment of the present invention having a tube with two balloons attached to that portion of the tube that is disposed within the patient's digestive system.

FIG. 8 illustrates a third embodiment of the present invention showing a tube having two balloons attached to that portion of the tube that is disposed within the patient's upper digestive system. The balloon anchor 2 is expandable to about 10 ml and is positioned up against the stomach wall to prevent the tube 1 from falling out. The inflatable balloon 29 is expandable from about 100 ml to about 850 ml and may be expanded intermittently to limit the capacity of the stomach. For example, the balloon 29 may be inflated via an inflation lumen prior to a meal to create the sensation of being full. After the meal, the balloon 29 may be deflated to prevent chronic accommodation. An electrically or a manually operated pump may be used to cause the inflation.

The tube 1 in this embodiment has a long inner tube length of about 10 cm or longer and a diameter of 28 French (9.3 mm) in size or greater. The tube 1 may have multiple holes 32 in the sidewall of its distal end portion 17 as shown in FIG. 8 and also in FIGS. 10 and 13-15B. The holes 32 may be 5×7 mm in size. The holes 32 provide non-vascular drainage from the patient. Preferably, the holes 32 are arranged in a spiral pattern 1 cm to 1.5 cm apart without losing structural integrity. More preferably, cushions or bumpers (not shown) are located on the tube 1 and in between the holes 32 to prevent the tube from being sucked up against the stomach wall while food is extracted from the upper digestive system out through the tube 1. For example, cushions or bumpers that are raised 3-4 mm above the surface of the tube 1 may be used for this purpose.

Figure 15A:
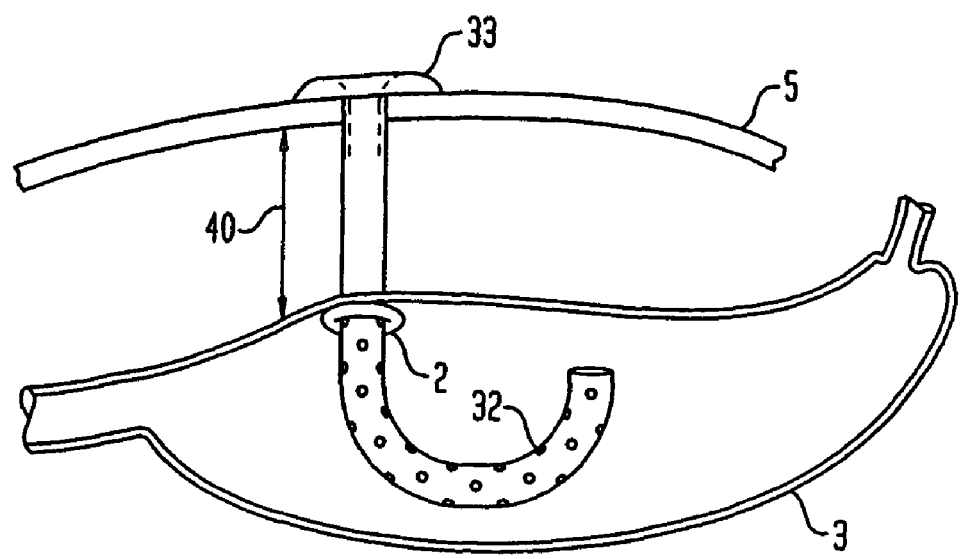
FIG. 15A and FIG. 15B are schematic views of an embodiment of the present invention installed in a patient illustrating how the apparatus accommodates changes in thickness of the abdominal wall of a patient.
Figure 15B:
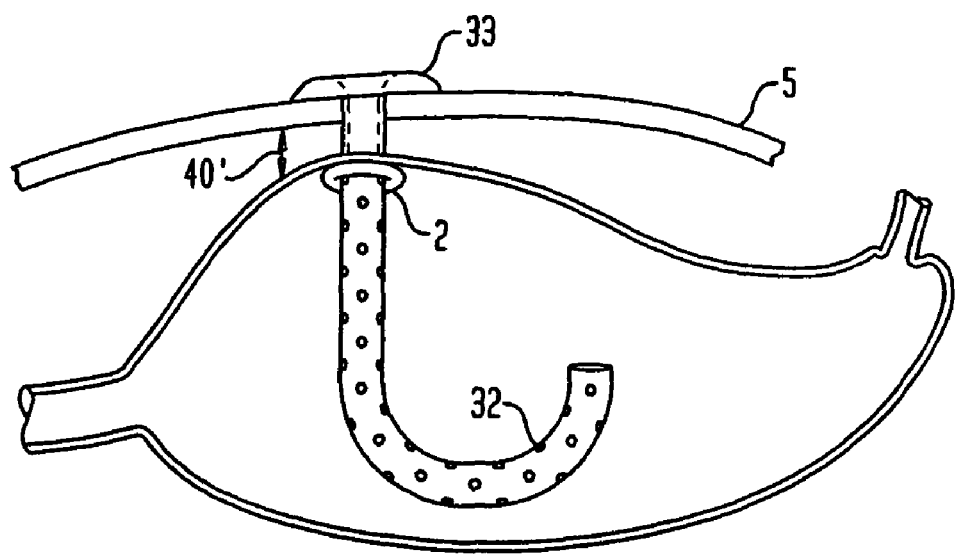

As shown in FIG. 8, a second retention member 33 may be attached at the proximal end portion 16 of the tube 1 to keep the tube 1 fixed to the abdominal surface. This second retention member may be similar to the retention members described hereinabove and shown in FIGS. 1, 1A, 1B and 6. The distance between the second retention member 33 at the proximal end portion 16 of the tube 1 and the balloon anchor 2 at the distal end portion 17 of the tube 1 can be adjusted to account for the varying amount of intervening tissue 40, 40' as shown in FIGS. 15A and 15B. For example, the second retention member 33 may be attached to the tube 1 via an interference or friction fit. Specifically, the second retention member 33 may be placed around the outer surface of the proximal end portion 16 of the tube 1 and held in place on the tube 1 if it has an inner diameter that is slightly smaller than the outer diameter of the tube 1. As the patient loses weight, the proximal end portion 16 of the tube 1 extends farther and farther away from the patient's abdominal surface. A physician or the patient can slide the second retention member 33 down towards the abdominal surface and the excess amount of the tube 1 can be cut off.

Figure 9:
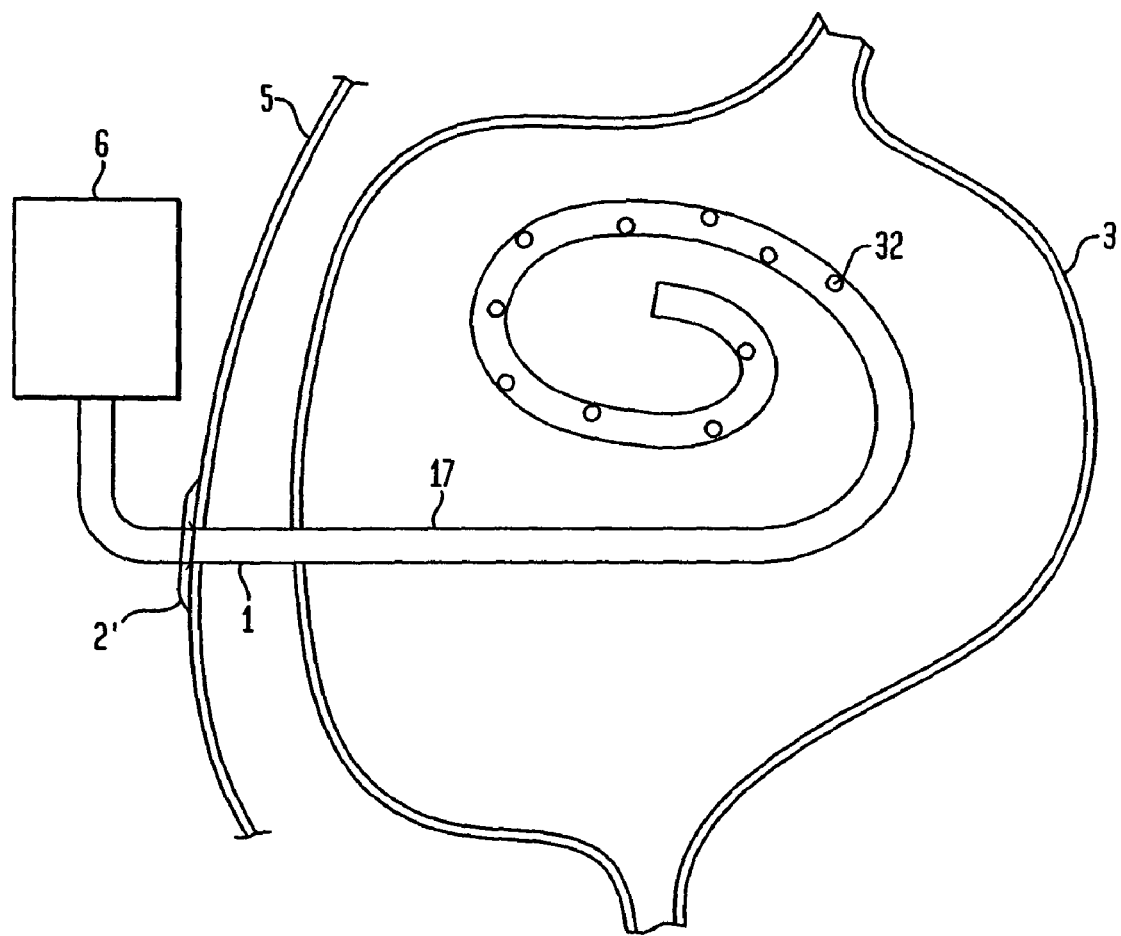
FIG. 9 is a schematic view of a fourth embodiment of the present invention having a tube with a curved configuration and a plurality of holes in a sidewall.
Figure 10:
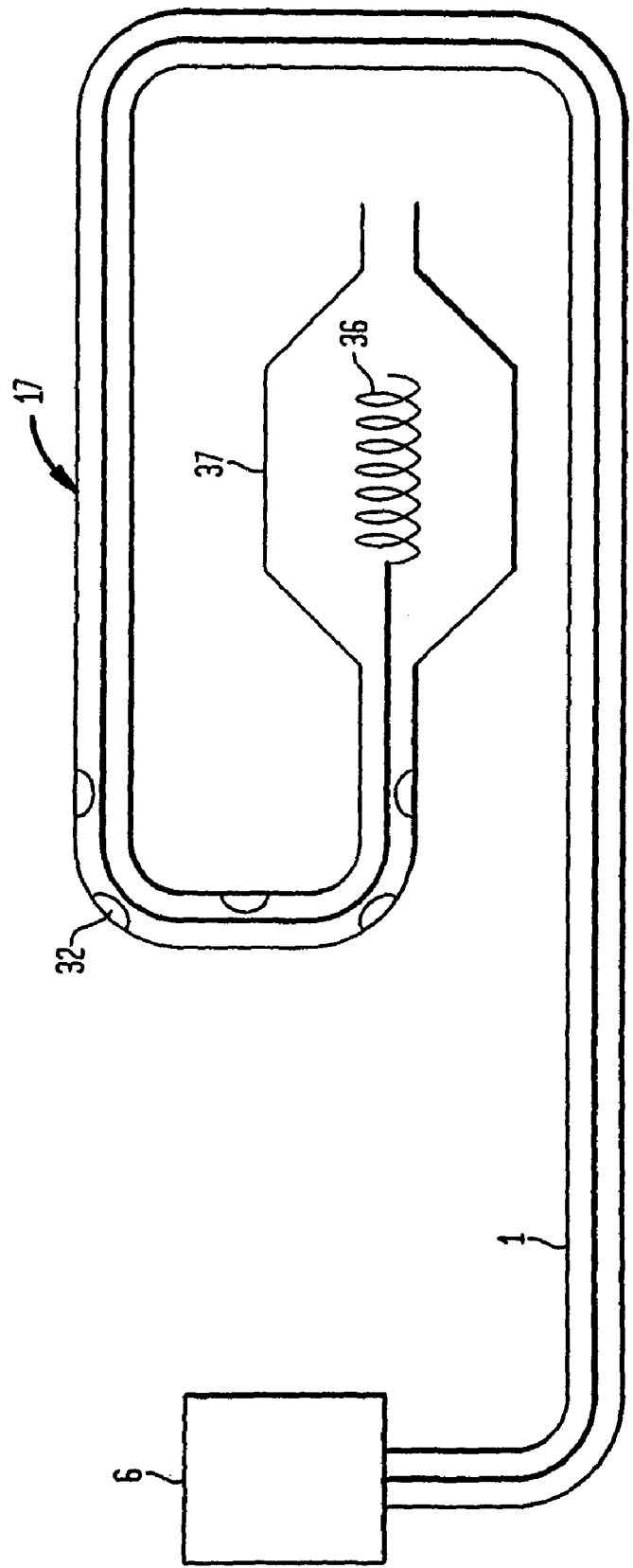
FIG. 10 is a schematic view of a fifth embodiment of the present invention having a tube with a curved configuration, multiple holes in a sidewall, and a morcellation device housed within a cage at its distal end portion.

FIG. 9 illustrates a fourth embodiment of the present invention with a tube 1 having a curved configuration at its distal end portion 17 and a plurality of holes 32 in a sidewall. As shown in FIG. 9, the distal end portion 17 of the tube 1 is adapted to assume a curved configuration when disposed in the upper digestive system of a patient. Specifically, the distal end portion 17 of the tube 1 is flexible to facilitate insertion and removal from the patient. When the distal end portion 17 of the tube 1 is disposed in the upper digestive system of the patient, it returns to its natural curved configuration. The tube's tendency to return to its natural curved configuration may be achieved, for example, by bending the tube into a desired curved shape during the manufacturing process before the tube has fully cured or cooled, or by incorporating shape memory materials into the tube. As used herein, the term "curved" includes flexed, bent, rounded, arched, curled, coiled, spiral, and pigtail. This curved configuration is preferable because it increases the intake area within the upper digestive system. In addition, the coiled distal end portion 17 of the tube 1 as shown in FIG. 10 helps to maintain the position of the tube 1 within the patient's upper digestive system. The distal end portion 17 of the tube 1 may, for example, be about 10 cm long or longer to improve the intake of the food from the upper digestive system. Retention members (not shown) similar to the ones described in the above embodiments may also be used in this embodiment.

In an alternative embodiment (not shown), an actuating mechanism is configured to bend the distal end portion 17 of the tube 1 into a curved configuration. The actuating mechanism may, for example, be a string attached to the distal end portion 17 of the tube 1 that, when retracted causes the tube to assume a curved configuration (e.g. a loop with an arc that measures between about 270°-360°). A Cope Loop is a well known example of this arrangement.

FIG. 10 illustrates a fifth embodiment of the present invention showing a tube 1 having a curved configuration, multiple holes 32 in a sidewall, and a morcellation device 36 housed within a housing 37 at its distal end portion 17. Examples of morcellation devices are disclosed in U.S. Pat. Nos. 5,618, 296, 5,741,287 and 5,520,634, herein incorporated by reference in their entirety. As shown in FIG. 10, a morcellation device 36 is provided at the distal end portion 17 of the tube 1 to divide and grind food into smaller pieces as it enters the tube 1. The morcellation device 36 thus allows large food to be removed from the patient without clogging the tube 1. The morcellation device 36 can be, for example, a mechanical propeller provided within a housing 37 at the distal end portion 17 of the tube 1. The housing 37 is constructed to protect body tissue from the morcellation device 36. In the illustrated embodiment, the housing 37 has an opening to permit the entry of food from the patient into the tube 1 and may, for example, be a cage that surrounds the morcellation device 36 at the distal end portion 17 of the tube 1. It is preferable that the housing 37 is collapsible in both directions so that it can be easily inserted into and taken out of the patient. The housing 37 is necessary to prevent damage to the stomach.

FIG. 11 illustrates a feature that may be used with any embodiment of the present invention in which the proximal end portion 16 of the tube 1 lies substantially flush with the outer surface of the patient's abdomen. This may be achieved by using ribbons attached to the tube 1, for example at the internal retention member. The ribbons are used to pull the tube 1 taut when the distal end portion 17 of the tube 1 is disposed in the upper digestive system of a patient. While the ribbons are pulled, the proximal end portion 16 of the tube 1 is cut so that the proximal end portion 16 lies flush with the abdominal surface and a thin, hollow cylinder with flanges is wedged onto the outside or inside surface of the tube 1 via friction or by screwing it onto the tube 1 to retain the tube 1 in its position and to keep it flush with the abdominal surface. In alternative embodiments, the proximal end portion 16 of the tube 1 may extend out past the abdominal surface by any desired length (e.g., 1-10 inches).

Figure 12:
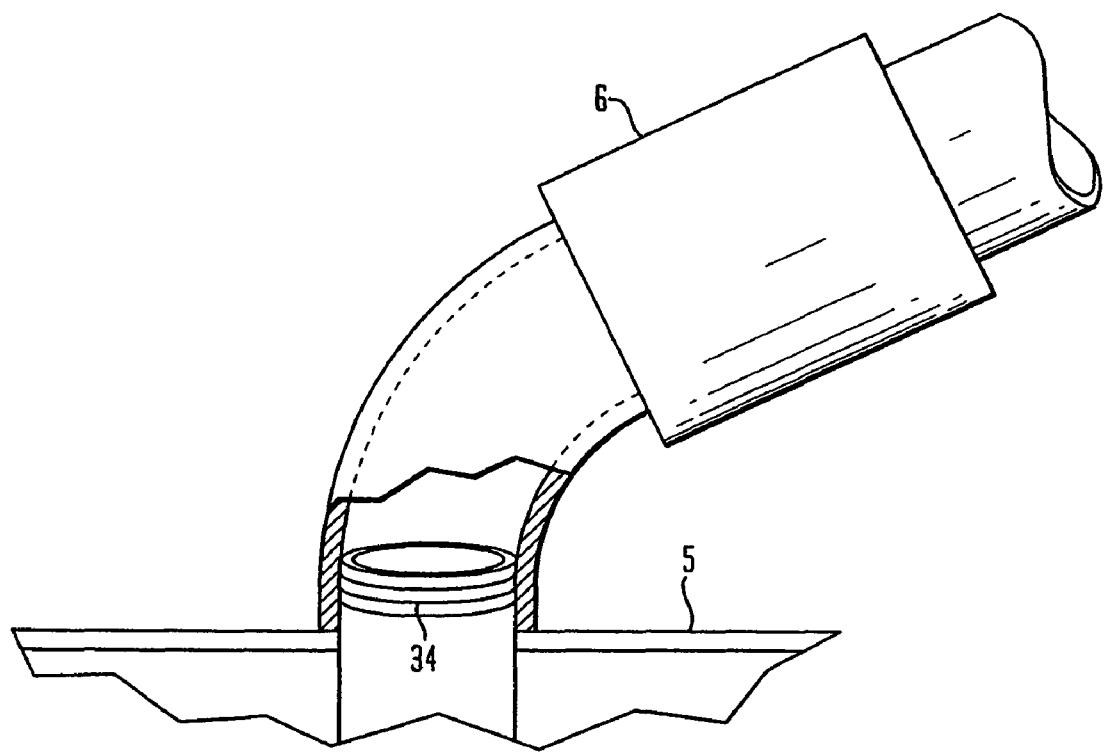
FIG. 12 is a schematic view of a luer lock at the proximal end portion of a tube.

FIG. 12 illustrates another feature that may be used with any embodiment of the present invention in which a luer lock 34 is utilized at the proximal end portion 16 of the tube 1. In this embodiment, the pump 6 is attached to the tube 1 by screwing the pump 6 onto the tube 1 around the external portion of the proximal end portion 16 of the tube 1 rather than being inserted into the tube 1. More specifically, the proximal end portion 16 of the tube 1 comprises concentric grooves or threads on the outside to accommodate the pump 6, which prevents the pump 6 from reducing the size of the removal lumen 25. Likewise, the pump 6 may have corresponding concentric grooves or threads that allow it to interact and connect with the luer lock 34. In this way, large pieces of food can still be extracted out of the tube 1 because the inner diameter of the tube 1 is not compromised or decreased due to the pump 6 being inserted into the tube 1. Instead, the pump 6 is coupled to or threaded onto the outside of the proximal end portion 16 of the tube 1.

Figure 13:
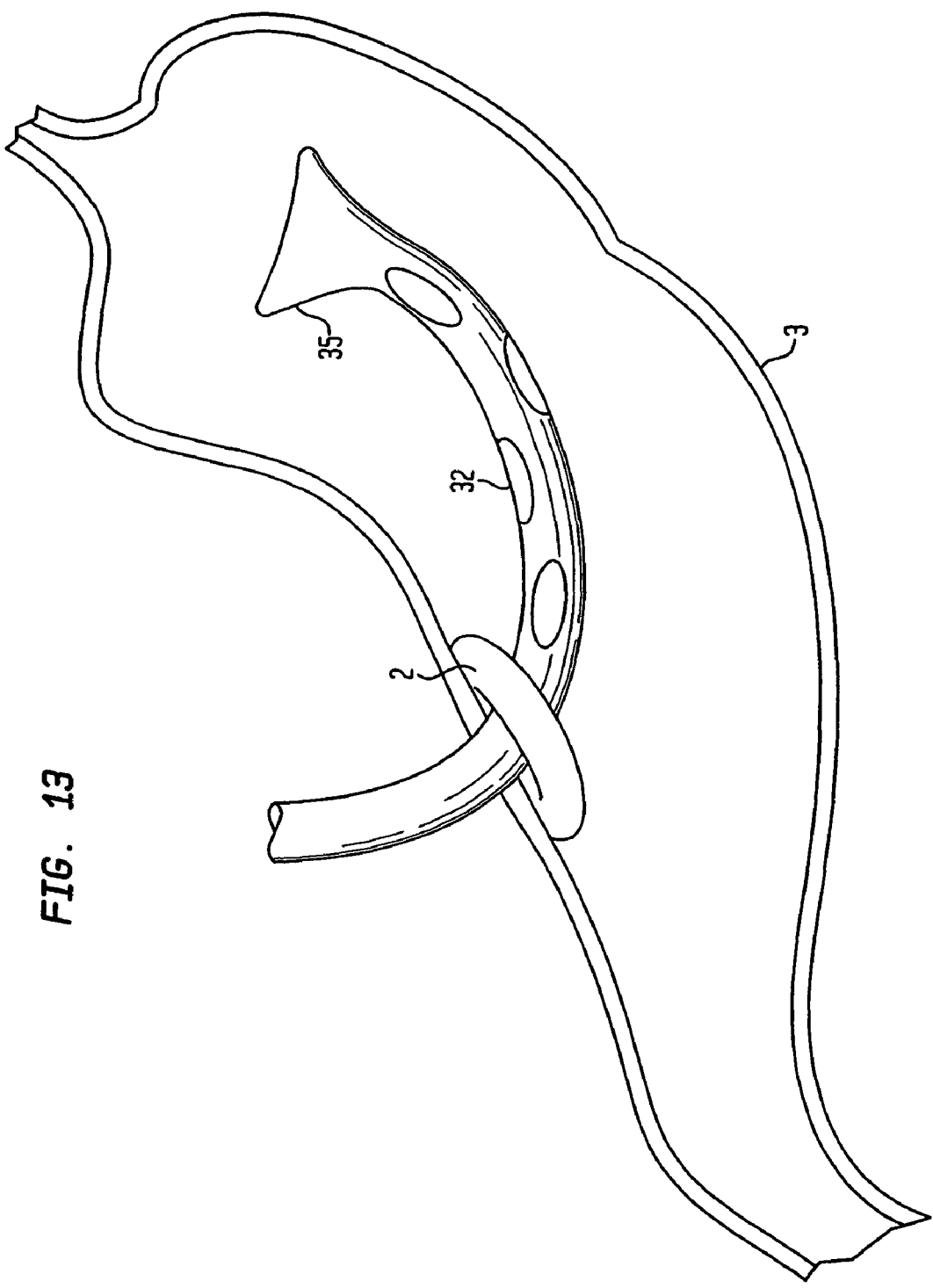
FIG. 13 is a schematic view of a variation of an embodiment of the present invention having a tube with a funnel shaped tip.

FIG. 13 illustrates yet another feature that may be used with any embodiment of the present invention in which the tube 1 has a funnel shaped tip 35. The funnel tip is advantageous because it facilitates the extraction of larger pieces of food into the tube 1 from the patient's digestive system.

Figure 14:
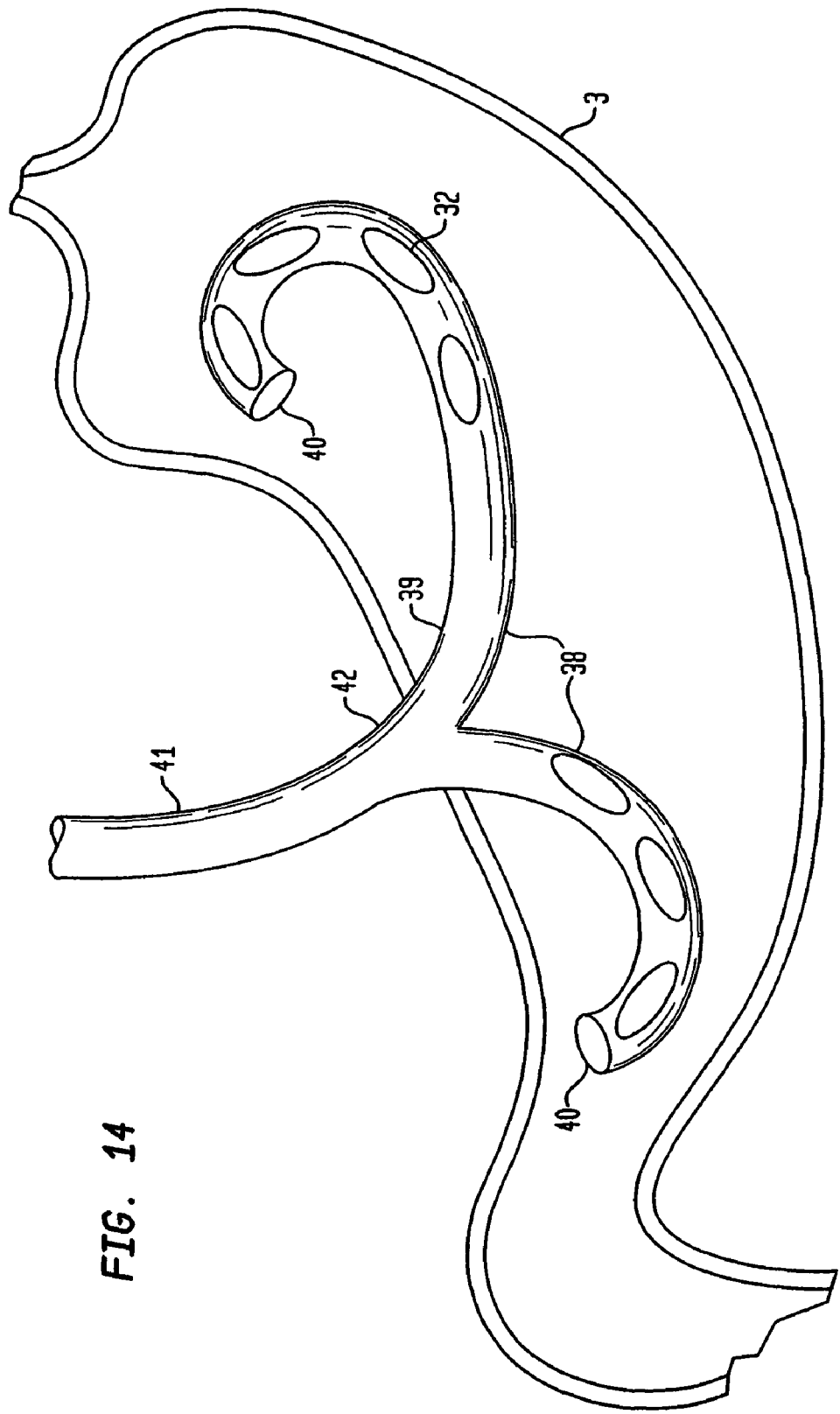
FIG. 14 is a schematic view of a sixth embodiment of the present invention having two intake tubes.

FIG. 14 illustrates a sixth embodiment of the present invention that has two intake tubes. In this embodiment, both of the intake tubes 38 have a curved configuration and a sidewall with a plurality of holes 32 located therein. Each intake tube 38 comprises a proximal end portion 39 and distal end portion 40. The apparatus also comprises an output tube 41 having a proximal end portion and a distal end portion 42. One or more retention members (not shown) are preferably attached to the output tube 41 to prevent the apparatus from coming out of the upper digestive system. The plurality of intake tubes 38 are configured to be disposed in the upper digestive system of the patient and the output tube 41 is configured to pass through the patient's abdominal wall when the plurality of intake tubes 38 are so disposed. The distal end portion 42 of the output tube 41 is operatively connected to the proximal end portion 39 of each of the plurality of intake tubes 38 so that food can be extracted from the upper digestive system of the patient through the distal end portion 40 of each of the plurality of intake tubes 38 and out through the proximal end portion of the output tube 41.

Optionally, pressure and/or flow sensors (not shown) may be placed on and/or in the tube 1. Pressure sensors placed on the tube 1 inside and outside the stomach 3 may be used to estimate the satiety of the patient. Alternatively or in addition to, flow sensors that are placed inside the tube 1 may be used to calculate the volume of food extracted through the tube 1.

Reference is now made to various methods for extracting food, for limiting absorption of food, and for treating obese patients.

Installation of any of the above-described embodiments forms a passageway into a patient's upper digestive system through the patient's abdominal wall. The patient is allowed to carry out his/her everyday affairs including ingesting food. After the patient has ingested food, the food is extracted by pumping it out of the upper digestive system through the passageway before it is completely digested. This method and the others described below are less invasive than the alternative surgical procedures for reducing weight, are easy to perform, easy to reverse and have successfully resulted in significant weight loss in obese patients.

In one method, a tube is positioned so that it passes through a patient's abdominal wall into his/her upper digestive system. The patient is allowed to go about his/her daily activities including ingesting food. After the patient has ingested the food, the food is extracted from the upper digestive system of the patient through the tube. The patient may eat and extract the eaten food from his/her upper digestive system through the tube repeatedly until a desired weight loss is attained. The food that has been extracted is not reintroduced into the patient. The tube may be kept in the patient's upper digestive system for extended periods of time (e.g., one month or more) while the eating/extracting is repeated numerous times (e.g., 20 times or more) while the tube is in place.

In a second method, a tube is positioned so that it passes through the obese patient's abdominal wall into his/her upper digestive system. The obese patient is allowed to go about his/her daily activities including ingesting food. After the obese patient has ingested the food, the food is extracted from the upper digestive system of the obese patient through the tube. The obese patient may eat and extract the eaten food from his/her upper digestive system through the tube repeatedly until the obese patient has lost at least 40 pounds. The food that has been extracted is not reintroduced back into the obese patient.

In a third method, a tube is positioned so that it passes through a patient's abdominal wall into the upper digestive system of the patient whose gastrointestinal tract is unobstructed. The term "unobstructed," as used herein, refers to a gastrointestinal tract that is not mechanically obstructed and is also not functionally obstructed. The patient is allowed to go about his/her daily activities including ingesting food. After the patient has ingested the food, the food is extracted from the upper digestive system of the patient through the tube. The patient may eat and extract the eaten food from his/her upper digestive system through the tube repeatedly until a desired weight loss is attained. The tube may be kept in the patient's upper digestive system for extended periods of time (e.g., one month or more) while the eating/extracting is repeated numerous times (e.g., 20 times or more) while the tube is in place.

Preliminary trials in human patients have been successful. For example, one female patient, middle aged and weighing 100 kilograms (approximately 220 pounds), had a tube installed in her stomach for 59 weeks and successfully lost 38.45 kilograms (approximately 85 pounds) without experiencing any serious adverse side effects. During the 59 weeks, the female patient aspirated after breakfast and lunch meals daily. She consumed meals without any fluids over approximately 30 minutes. At the end of the meal, she consumed 52 ounces of water in approximately 3-4 minutes. She waited approximately 20 minutes after consuming the water before beginning the extraction procedure. Accordingly, the patient uncapped the tube, connected a 60 cc syringe to the tube and extracted food from her stomach twice. This resulted in a siphon effect, which permitted the subject to freely drain the stomach by allowing the open tube to empty into a bucket. The patient squeezed the tube to enhance propulsion and to break up large food. After draining stopped, the patient usually drank another 52 ounces of water and repeated the extraction procedure. She usually repeated this procedure (drinking and extracting) about 2 more times, until she felt her stomach was empty. The total amount of food extracted was approximately 2-3 liters and the entire procedure took about 20 minutes. If resistance to extraction occurred during the procedure, the patient flushed the tube with 30 cc of water. The water helped to extract the food by dissolving it and by cleaning the passageway. The patient changed her dietary intake to avoid tube clogging. She avoided eating cauliflower, broccoli, Chinese food, stir fry, snow peas, pretzels, chips, and steak. In addition, her diet was supplemented with potassium. The chart below illustrates her weight loss.

| Week | weight (kg) |
|---|---|
| 0 | 100.9 |
| 2 | 96.8 |
| 3 | 96.8 |
| 4 | 94.7 |

-continued

| Week | weight (kg) |
|---|---|
| 4 | 94.7 |
| 5 | 94.0 |
| 7 | 93.6 |
| 8 | 90.9 |
| 9 | 92.9 |
| 10 | 92.7 |
| 11 | 90.4 |
| 12 | 89 |
| 13 | 89.3 |
| 14 | 88.6 |
| 15 | 87.7 |
| 16 | 86.5 |
| 17 | 86.5 |
| 18 | 86.3 |
| 19 | 85.9 |
| 20 | 83.9 |
| 21 | 82.9 |
| 22 | 81.6 |
| 23 | 80.45 |
| 24 | 79.7 |
| 25 | 78.6 |
| 26 | 78.6 |
| 27 | 77.2 |
| 28 | 78 |
| 29 | 76.2 |
| 30 | 76 |
| 31 | 75.2 |
| 31 | 77.1 |
| 32 | 76.4 |
| 33 | 76.4 |
| 34 | 76.4 |
| 35 | 74 |
| 36 | 74 |
| 37 | 74 |
| 38 | 73.6 |
| 39 | 73.5 |
| 40 | 73.2 |
| 41 | 72.6 |
| 42 | 71.22 |
| 43 | 69.5 |
| 44 | 69.8 |
| 45 | 69.45 |
| 46 | 68.45 |
| 47 | 66.6 |
| 48 | 65.5 |
| 49 | 65.5 |
| 50 | 65.5 |
| 51 | 65.2 |
| 52 | 65 |
| 53 | 65 |
| 54 | 64.5 |
| 55 | 64.8 |
| 56 | 64.8 |
| 57 | 63.8 |
| 58 | 63 |
| 59 | 62.45 |

It is noted that the food extraction apparatuses and methods described above are preferably combined with a behavior modification program that ideally educates patients in modifying caloric intake, lifestyle and attitudes toward food. Learned activities and support for weight loss may include activities such as self-monitoring by recording food intake and physical activity, avoiding triggers that prompt eating, assistance from family and friends, problem solving skills and relapse prevention. The program may be taught by an instructor or offered over the internet. In addition, the program preferably includes a series of regular check-ups by a health care provider. The check-ups ideally include regularly testing blood for electrolytes, supplementing patients' diets with vitamins, and administering medications to prevent gallstone formation as needed. Ideally, the behavior modification program will educate patients to change their lifestyle so as to eliminate the need for food extraction.

The above described embodiments allow obese patients to lose weight without undergoing drastic and invasive surgeries. As a result, obese patients avoid many of the complications associated with such surgeries. In addition, the present invention is easy to perform, easy to reverse and allows obese patients to live a normal and active lifestyle with fewer adverse side effects.

Additional advantages and modifications will readily occur to those skilled in the art. For example, the features of any of the embodiments may be used singularly or in combination with any other of the embodiments of the present invention. In addition, the insertion technique for placing the tube is not limited to known gastrostomy techniques. Accordingly, various modifications may be made without departing from the spirit or scope of the general inventive concept as defined by the appended claims and their equivalents.

We claim:

1. A method of achieving weight loss in a patient comprising the steps of:
   (a) positioning a tube that passes through the patient's abdominal wall into the patient's stomach, wherein the patient's gastrointestinal tract is unobstructed;
   (b) allowing the patient to ingest food and allowing the ingested food to accumulate in the patient's stomach;
   (c) waiting until after the patient has finished ingesting the food and subsequently extracting the food from the patient's stomach through the tube; and
   (d) repeating steps (b) and (c) until the patient has lost at least 40 pounds.

2. The method of claim 1, wherein the food that has been extracted in step (c) is not reintroduced into the patient.

3. The method of claim 1, wherein the tube is inserted by percutaneous endoscopic, radiological or surgical methods.

4. The method of claim 1, wherein the waiting step comprises waiting about 20 minutes.

5. The method of claim 1, wherein in step (c), the food is extracted by pumping the food out of the patient's stomach through the tube.

6. The method of claim 1, further comprising the step of monitoring how much food is extracted in step (c).

7. The method of claim 1, further comprising the step of monitoring the patient's biochemical/nutritional status and the weight loss attained.

8. The method of claim 1, further comprising the step of removing the tube (i) by pulling the tube out of the patient using traction, (ii) by endoscopy or (iii) by surgery.

9. The method of claim 1, further comprising the steps of:
   (e) educating the patient to modify caloric intake and lifestyle;
   (f) regularly testing the patient's blood for electrolytes;
   (g) supplementing the patient's diet with vitamins and minerals as needed; and
   (h) administering medication to the patient to prevent gallstone formation as needed.

10. The method of claim 1, wherein the waiting step comprises waiting about 20 minutes, and wherein in step (c), the food is extracted by pumping the food out of the stomach through the tube.

11. A method of limiting absorption of food comprising the steps of:
   (a) positioning a tube that passes through a patient's abdominal wall into a patient's stomach, wherein the patient's gastrointestinal tract is unobstructed;
   (b) allowing the patient to ingest food and allowing the ingested food to accumulate in the patient's stomach;
   (c) waiting until after the patient has finished ingesting the food and subsequently extracting the food from the patient's stomach through the tube; and
   (d) keeping the tube in the patient for at least one month and repeating steps (b) and (c) at least 20 times to achieve weight loss in the patient.

12. The method of claim 11, wherein the food that has been extracted in step (c) is not reintroduced into the patient.

13. The method of claim 11, wherein the waiting step comprises waiting about 20 minutes.

14. The method of claim 11, wherein in step (c), the food is extracted by pumping the food out of the patient's stomach through the tube.

15. The method of claim 11, wherein the waiting step comprises waiting about 20 minutes, and wherein in step (c), the food is extracted by pumping the food out of the stomach through the tube.

16. A method of achieving weight loss in a patient comprising the steps of:
   (a) introducing a passageway into a stomach of a patient whose gastrointestinal tract is unobstructed such that the passageway passes through the patient's abdominal wall;
   (b) allowing the patient to ingest food and allowing the ingested food to accumulate in the patient's stomach;
   (c) waiting until after the patient has finished ingesting the food and subsequently extracting the food from the patient's stomach through the passageway; and
   (d) repeating steps (b) and (c) until the patient has lost at least 40 pounds.

17. The method of claim 16, wherein the food that has been extracted in step (c) is not reintroduced into the patient.

18. A method of limiting absorption of food comprising the steps of:
   (a) introducing a passageway into a stomach of a patient whose gastrointestinal tract is unobstructed such that the passageway passes through the patient's abdominal wall;
   (b) allowing the patient to ingest food and allowing the ingested food to accumulate in the patient's stomach;
   (c) waiting until after the patient has finished ingesting the food and subsequently extracting the food from the patient's stomach through the passageway; and
   (d) repeating steps (b) and (c) at least 20 times to achieve weight loss in the patient.

19. The method of claim 18, wherein the food that has been extracted in step (c) is not reintroduced into the patient.

20. A method of achieving weight loss in a person having a passageway into the person's stomach that passes through the person's abdominal wall, the method comprising the steps of:
   (a) ingesting food and allowing the ingested food to accumulate in the person's stomach;
   (b) waiting until after the person has finished ingesting the food and subsequently extracting the food from the person's stomach through the passageway; and
   (c) repeating steps (a) and (b) until the person has lost at least 40 pounds,
wherein the patient's gastrointestinal tract is unobstructed.

21. The method of claim 20, wherein the food that has been extracted in step (b) is not reintroduced into the person.

22. The method of claim 20, wherein in step (b), the food is extracted by pumping the food out of the person's stomach through the passageway.

23. The method of claim 20, wherein steps (a) and (b) are repeated at least 20 times.

24. A method of limiting absorption of food in a person having a passageway into the person's stomach that passes through the person's abdominal wall, the method comprising the steps of:
 (a) ingesting food and allowing the ingested food to accumulate in the person's stomach;
 (b) waiting until after the person has finished ingesting the food and subsequently extracting the food from the person's stomach through the passageway; and
 (c) repeating steps (a) and (b) at least 20 times to achieve weight loss in the person,
wherein the patient's gastrointestinal tract is unobstructed.

25. The method of claim 24, wherein the food that has been extracted in step (b) is not reintroduced into the person.

26. The method of claim 24, wherein in step (b), the food is extracted by pumping the food out of the person's stomach through the passageway.

27. A method of achieving weight loss in a patient comprising the steps of:
 (a) introducing a passageway into a stomach of a patient whose gastrointestinal tract is unobstructed such that the passageway passes through the patient's abdominal wall;
 (b) allowing the patient to ingest food;
 (c) extracting the food from the patient's stomach through the passageway, wherein initiation of the extracting step occurs after the ingested food has accumulated in the patient's stomach and after the patient has finished ingesting the food; and
 (d) repeating steps (b) and (c) until the patient has lost at least 40 pounds.

28. The method of claim 27, wherein initiation of the extracting step occurs about 20 minutes after the patient has finished ingesting the food.

29. The method of claim 27, wherein the introducing step comprises positioning a tube that passes through the patient's abdominal wall into the patient's stomach.

30. The method of claim 27, wherein the food that has been extracted in step (c) is not reintroduced into the patient.

31. A method of limiting absorption of food comprising the steps of:
 (a) introducing a passageway into a stomach of a patient whose gastrointestinal tract is unobstructed such that the passageway passes through the patient's abdominal wall;
 (b) allowing the patient to ingest food;
 (c) extracting the food from the patient's stomach through the passageway, wherein initiation of the extracting step occurs after the ingested food has accumulated in the patient's stomach and after the patient has finished ingesting the food; and
 (d) keeping the tube in the patient for at least one month and repeating steps (b) and (c) at least 20 times to achieve weight loss in the patient.

32. The method of claim 31, wherein initiation of the extracting step occurs about 20 minutes after the patient has finished ingesting the food.

33. The method of claim 31, wherein the introducing step comprises positioning a tube that passes through the patient's abdominal wall into the patient's stomach.

34. The method of claim 31, wherein the food that has been extracted in step (c) is not reintroduced into the patient.

35. A method of achieving weight loss in a person having a passageway into the person's stomach that passes through the person's abdominal wall, the method comprising the steps of:
 (a) ingesting food;
 (b) extracting the food from the person's stomach through the passageway, wherein initiation of the extracting step occurs after the ingested food has accumulated in the person's stomach and after the patient has finished ingesting the food; and
 (c) repeating steps (a) and (b) until the person has lost at least 40 pounds,
wherein the patient's gastrointestinal tract is unobstructed.

36. The method of claim 35, wherein initiation of the extracting step occurs about 20 minutes after the person has finished ingesting the food.

37. The method of claim 35, wherein the food that has been extracted in step (b) is not reintroduced into the person.

38. A method of limiting absorption of food in a person having a passageway into the person's stomach that passes through the person's abdominal wall, the method comprising the steps of:
 (a) ingesting food;
 (b) extracting the food from the person's stomach through the passageway, wherein initiation of the extracting step occurs after the ingested food has accumulated in the person's stomach and after the patient has finished ingesting the food; and
 (c) repeating steps (a) and (b) at least 20 times to achieve weight loss,
wherein the patient's gastrointestinal tract is unobstructed.

39. The method of claim 38, wherein initiation of the extracting step occurs about 20 minutes after the person has finished ingesting the food.

40. The method of claim 38, wherein the food that has been extracted in step (b) is not reintroduced into the person.

41. A method of achieving weight loss in a patient comprising the steps of:
 (a) introducing a passageway into a stomach of a patient whose gastrointestinal tract is unobstructed such that the passageway passes through the patient's abdominal wall;
 (b) allowing the patient to ingest food and allowing the ingested food to accumulate in the patient's stomach;
 (c) waiting for partial digestion of the ingested food to occur in the patient's stomach, and subsequently extracting the food from the patient's stomach through the passageway; and
 (d) repeating steps (b) and (c) until the patient has lost at least 40 pounds.

42. The method of claim 41, wherein the waiting step comprises the step of waiting about 20 minutes after the patient has finished ingesting the food.

43. The method of claim 41, wherein the introducing step comprises positioning a tube that passes through the patient's abdominal wall into the patient's stomach.

44. The method of claim 41, wherein the food that has been extracted in step (c) is not reintroduced into the patient.

45. A method of limiting absorption of food comprising the steps of:
 (a) introducing a passageway into a stomach of a patient whose gastrointestinal tract is unobstructed such that the passageway passes through the patient's abdominal wall;
 (b) allowing the patient to ingest food and allowing the ingested food to accumulate in the patient's stomach;
 (c) waiting for partial digestion of the ingested food to occur in the patient's stomach, and subsequently extracting the food from the patient's stomach through the passageway; and (d) keeping the tube in the patient for at least one month and repeating steps (b) and (c) at least 20 times to achieve weight loss in the patient.

46. The method of claim 45, wherein the waiting step comprises the step of waiting about 20 minutes after the patient has finished ingesting the food.

47. The method of claim 45, wherein the introducing step comprises positioning a tube that passes through the patient's abdominal wall into the patient's stomach.

48. The method of claim 45, wherein the food that has been extracted in step (c) is not reintroduced into the patient.

49. A method of achieving weight loss in a person having a passageway into the person's stomach that passes through the person's abdominal wall, the method comprising the steps of:

(a) ingesting food and allowing the ingested food to accumulate in the person's stomach;

(b) waiting for partial digestion of the ingested food to occur in the person's stomach, and subsequently extracting the food from the person's stomach through the passageway; and (c) repeating steps (a) and (b) until the person has lost at least 40 pounds, wherein the patient's gastrointestinal tract is unobstructed.

50. The method of claim 49, wherein initiation of the extracting step occurs about 20 minutes after the person has finished ingesting the food.

51. The method of claim 49, wherein the food that has been extracted in step (b) is not reintroduced into the person.

52. A method of limiting absorption of food in a person having a passageway into the person's stomach that passes through the person's abdominal wall, the method comprising the steps of:

(a) ingesting food and allowing the ingested food to accumulate in the person's stomach;

(b) waiting for partial digestion of the ingested food to occur in the person's stomach, and subsequently extracting the food from the person's stomach through the passageway; and (c) repeating steps (a) and (b) at least 20 times to achieve weight loss, wherein the patient's gastrointestinal tract is unobstructed.

53. The method of claim 52, wherein initiation of the extracting step occurs about 20 minutes after the person has finished ingesting the food.

54. The method of claim 52, wherein the food that has been extracted in step (b) is not reintroduced into the person.

* * * * *